United States Patent
Gilboa et al.

(10) Patent No.: US 7,785,583 B2
(45) Date of Patent: Aug. 31, 2010

(54) IN SITU MATURATION OF DENDRITIC CELLS

(75) Inventors: Eli Gilboa, Durham, NC (US); Smita Nair, Durham, NC (US)

(73) Assignees: Argos Therapeutics, Inc., Durham, NC (US); Duke University, Durham, NC (US)

( * ) Notice: Subject to any disclaimer, the term of this patent is extended or adjusted under 35 U.S.C. 154(b) by 631 days.

(21) Appl. No.: 10/536,211

(22) PCT Filed: Dec. 10, 2003

(86) PCT No.: PCT/US03/39239

§ 371 (c)(1),
(2), (4) Date: Dec. 6, 2005

(87) PCT Pub. No.: WO2004/053095

PCT Pub. Date: Jun. 24, 2004

(65) Prior Publication Data

US 2006/0121003 A1    Jun. 8, 2006

Related U.S. Application Data

(60) Provisional application No. 60/432,224, filed on Dec. 10, 2002.

(51) Int. Cl.
*A01N 63/00* (2006.01)
*A61K 45/00* (2006.01)
*A61K 47/00* (2006.01)

(52) U.S. Cl. .................... 424/93.71; 424/278.1

(58) Field of Classification Search ........... None
See application file for complete search history.

(56) References Cited

U.S. PATENT DOCUMENTS

| 5,853,719 | A | 12/1998 | Nair et al. |
| 2001/0007659 | A1 | 7/2001 | Wong-Staal et al. |
| 2002/0041869 | A1* | 4/2002 | Ali et al. ............ 424/93.21 |
| 2003/0139364 | A1* | 7/2003 | Krieg et al. ............ 514/44 |

OTHER PUBLICATIONS

Fallarino et al., 1999, Int. J. Cancer, vol. 80P: 324-333.*
Janeway and Travers, 1997, Immunobiology, pp. 7:12-7:13.*
Candido et al., 2001, Canc. Res. vol. 61: 228-236.*
Sauder et al., 2000, J. Am. Acad. Dermatol. vol. 43: s6-S11.*
Smith et al., 1966, S.A. Med. Journal., p. 1125.*
Burdin et al., 2001, Cell Biol and Toxico. vol. 17: 67-75.*
Suzuki et al., 2000, J Ivest. Derm. vol. 114: 135-141.*
Trevejo et al., 2001, PNAS< vol. 98: 12162-12167.*
Australian Patent Office Examiner's Report dated Oct. 10, 2007 for Australian Patent Application No. 2003296439.
Merad et al., "In Vivo Manipulation of Dendritic Cells to Induce Therapeutic Immunity", *Blood*, vol. 99 (5); pp. 1676-1682, Mar. 1, 2002.
Suzuki et al., "Imiquimod, a Topical Immune Response Modifier, Induces Migration of Langerhans Cells", *Journal of Investigative Dermatology*, vol. 114 (1); pp. 135-141, Jan. 2000.
International Preliminary Examination Report for corresponding PCT Application No. PCT/US03/39239 dated Jun. 9, 2005.
International Search Report for corresponding PCT Application No. PCT/US03/39239 dated Sep. 10, 2004.
Official Action corresponding to Australian Patent Application No. 2003296439 dated Dec. 17, 2008.

* cited by examiner

*Primary Examiner*—Amy E Juedes
(74) *Attorney, Agent, or Firm*—Jenkins, Wilson, Taylor & Hunt, P.A.

(57) ABSTRACT

A method for eliciting an immune response to an antigen in a subject via (a) loading isolated antigen presenting cells with an antigen ex vivo; and (b) administering the antigen presenting cells to a subject at a pre-treated site.

11 Claims, 6 Drawing Sheets

IN SITU MATURATION OF DENDRITIC CELLS

RELATED APPLICATIONS

This application is the national phase entry under 35 U.S.C. 371 of PCT application number PCT/US03/39239, filed Dec. 10, 2003, which claims the benefit of U.S. Provisional Patent Application Ser. No. 60/432,224, filed Dec. 10, 2002, the disclosure of which is incorporated herein by reference in its entirety.

TECHNICAL FIELD

The present invention generally relates to a method for eliciting an immune response in a subject. More particularly, the present invention provides a method for in situ maturation of antigen presenting cells for use in generating an immune response in a subject in which the generation of an immune response is desired.

Table of Abbreviations

| | |
|---|---|
| Ag | antigen |
| APC | antigen presenting cell |
| BRMs | biological response modifiers |
| CFSE | carboxyfluorescein succinimidyl ester |
| CTL | cytotoxic T lymphocyte |
| DC | dendritic cell |
| DTH | delayed-type hypersensitivity |
| Fc | antibody antigen-binding fragment |
| FITC | fluorescein isothiocyanate |
| GM-CSF | granulocyte macrophage colony-stimulating factor |
| HSP | heat shock protein |
| iDC | immature dendritic cell |
| IFN-α | interferon alpha |
| Ig | immunoglobulin |
| IL | interleukin |
| mDC | mature dendritic cell |
| MHC | major histocompatability complex |
| MIP | monocyte inflammatory protein |
| OVA | chicken ovalbumin |
| PGE | prostaglandin $E_2$ |
| poly-arg | poly arginine |
| Th1 | T Helper Type 1 |
| Th2 | T Helper Type 2 |
| TNF-α | tumor necrosis factor alpha |

BACKGROUND ART

Dendritic cells (DCs) are specialized for presenting antigens to naive or quiescent T cells. Consequently, DCs play a central role in modulating immunity in vivo (Steinman, 1991; Banchereau et al., 2000). Immunization using DCs loaded with selected antigens represents a powerful method of inducing immunity against pathogens or tumors (Gilboa et al., 1998; Dallal & Lotze, 2000; Fong & Engleman, 2000). Under appropriate conditions, DCs can also tolerize T cells and hence suppress an immune response against specific antigens (Steinman et al., 2000; Hackstein et al., 2001; Jonuleit et al., 2001).

The ability of DCs to induce an immune response requires antigen uptake, which occurs principally in non-lymphoid organs, followed by antigen presentation and activation of T cells in the lymph system. These separate functional roles are performed by immature DCs and mature DCs, respectively.

The signals for DC maturation are generally referred to as danger signals because they signal to the host the presence of a pathogen. Representative danger signals include various cytokines (e.g., IL-6, IL-1 or TNF-α), conserved pathogen determinants such as lipopolysaccharide (LPS), unmethylated CpG containing bacterial DNA, double stranded RNA, and components of cell debris such as heat shock proteins (HSP). See Celia et al. (1997) *Curr Opin Immunol* 9:10-16; Banchereau & Steinman (1998) *Nature* 392:245-252; Banchereau et al.(2000) *Annu Rev Immunol* 18:767-811; and Bell et al. (1999) *Adv Immunol* 72:255-324. Mature DCs are superior to immature DCs at eliciting an immune response (Morse et al., 1998; Nair et al., 1998). Immature DCs can also differentiate into tolerizing DCs, which disable cognate T cells from developing into an effector cell (Steinman et al., 2000; Hackstein et al., 2001; Jonuleit et al., 2001).

To elicit protective immunity, antigens of conventional vaccine formulations include: (a) protein; (b) attenuated or killed virus; (c) plasmid DNA; and (d) viral vectors. Optionally, a vaccine formulation also includes an adjuvant. Following administration of the vaccine to a subject, the antigen is captured by tissue resident immature DCs, which then mature.

More recently, vaccination strategies have been developed that accomplish antigen loading and maturation of DCs ex vivo. See e.g., Fong & Engleman (2000) *Annu Rev Immunol* 18:245-273. A typical approach for DC-based vaccination involves: (a) isolating and generating immature DCs from a subject; (b) loading the immature DCs with antigen; (c) culturing the immature DC in the presence of cytokines such as TNF-α, IL-6, IL-1β, and $PGE_2$, whereby the immature DC undergoes maturation; and (d) re-administering the antigen-loaded, mature DC to the subject (Romani et al., 1994; Sallusto & Lanzavecchia, 1994).

Multiple factors contribute to the generation of an appropriate microenvironment conducive for optimal DC maturation, however, these factors remain poorly characterized and it is unclear whether provision of maturation agents in vitro faithfully recapitulates the inflammatory microenvironment that generates mature DCs in vivo.

Thus, there exists a long-felt need in the art to develop methods for immunization using DCs. To meet such a need, the present invention provides a method for preparing DCs that involves in situ DC maturation. Specifically, the method involves administering antigen-loaded DCs to a subject at a site of inflammation, to thereby promote DC maturation in situ. The present invention offers significant advantages over existing methods for DC-based immunization, including: (a) induction of DC maturation that more closely mimics endogenous DC maturation; and (b) elimination of procedural steps and reagents required for maturation of DCs ex vivo.

SUMMARY OF THE INVENTION

The present invention discloses a method for eliciting an immune response in a subject. The, method comprises: (a) loading isolated antigen presenting cells with an antigen, wherein the loading is performed ex vivo; and (b) administering the antigen presenting cells to a subject at a pre-treated site, whereby an immune response to the antigen is generated in the subject.

In one embodiment, the antigen presenting cells are autologous to the subject. In one embodiment a subjects is a mammal. In another embodiment, a subject is a human.

Antigen presenting cells used in the methods of the invention include in one embodiment dendritic cells, and in another embodiment immature dendritic cells. The dendritic cells are loaded with an antigen, which can comprise an exogenous antigen or a self antigen.

In accordance with the present invention, the antigen-loaded dendritic cells are administered to a subject at a pre-treated site. The pre-treated site can be a site of inflammation or a site that has been induced to undergo an inflammation-like response. Inflammation can be generated by administration of a biological response modifier. In one embodiment, a biological response modifier is an adjuvant. In one embodiment, an adjuvant used in the methods of the invention is a Th1-inducing adjuvant. In another embodiment, an adjuvant used in the methods of the invention is a Th2-inducing adjuvant. In one embodiment, a vasodilator is administered to provide pre-treatment of the site.

In accordance with the present invention, a biological response modifier (e.g. an adjuvant) is administered to a site contemporaneously with, or prior to, administration of antigen presenting cells. Time periods for administering adjuvant include in one embodiment 0-15 minutes, in another embodiment 15-60 minutes, in another embodiment 1-3 hours, in another embodiment 3-5 hours, in another embodiment 5-8 hours, and in still another embodiment more than 8 hours prior to administration of antigen presenting cells.

The present invention provides that an immune response is elicited in the subject by performance of the disclosed method. An immune response can comprise an immunostimulatory response or an immunosuppressive response (e.g., a tolerizing immune response).

Accordingly, it is an object of the present invention to provide a method for eliciting an immune response via administration and in situ maturation of antigen presenting cells. This object is achieved in whole or in part by the present invention.

An object of the invention having been stated above, other objects and advantages of the present invention will become apparent to those skilled in the art after a study of the following description of the invention.

BRIEF DESCRIPTION OF THE DRAWINGS

FIG. 1A is a schematic diagram that outlines a prior art method for ex vivo maturation of DCs. Ex vivo maturation of DCs requires two steps prior to administration of the DCs: (1) preparation of immature DCs, which can be loaded with antigen; and (2) administration of maturation agents to the immature DCs, whereby the immature DCs become mature DCs.

FIG. 1B is a schematic diagram that outlines representative methods for in situ maturation of DCs, as provided by the present invention and disclosed herein. In situ maturation of DCs is a simplified procedure that requires only a single manipulation of DCs prior to administration to a subject. According to this approach, immature DCs are administered to a subject at a site of inflammation, whereby the immature DCs are induced to mature in situ.

DETAILED DESCRIPTION OF THE INVENTION

I. Definitions

Figure 1:
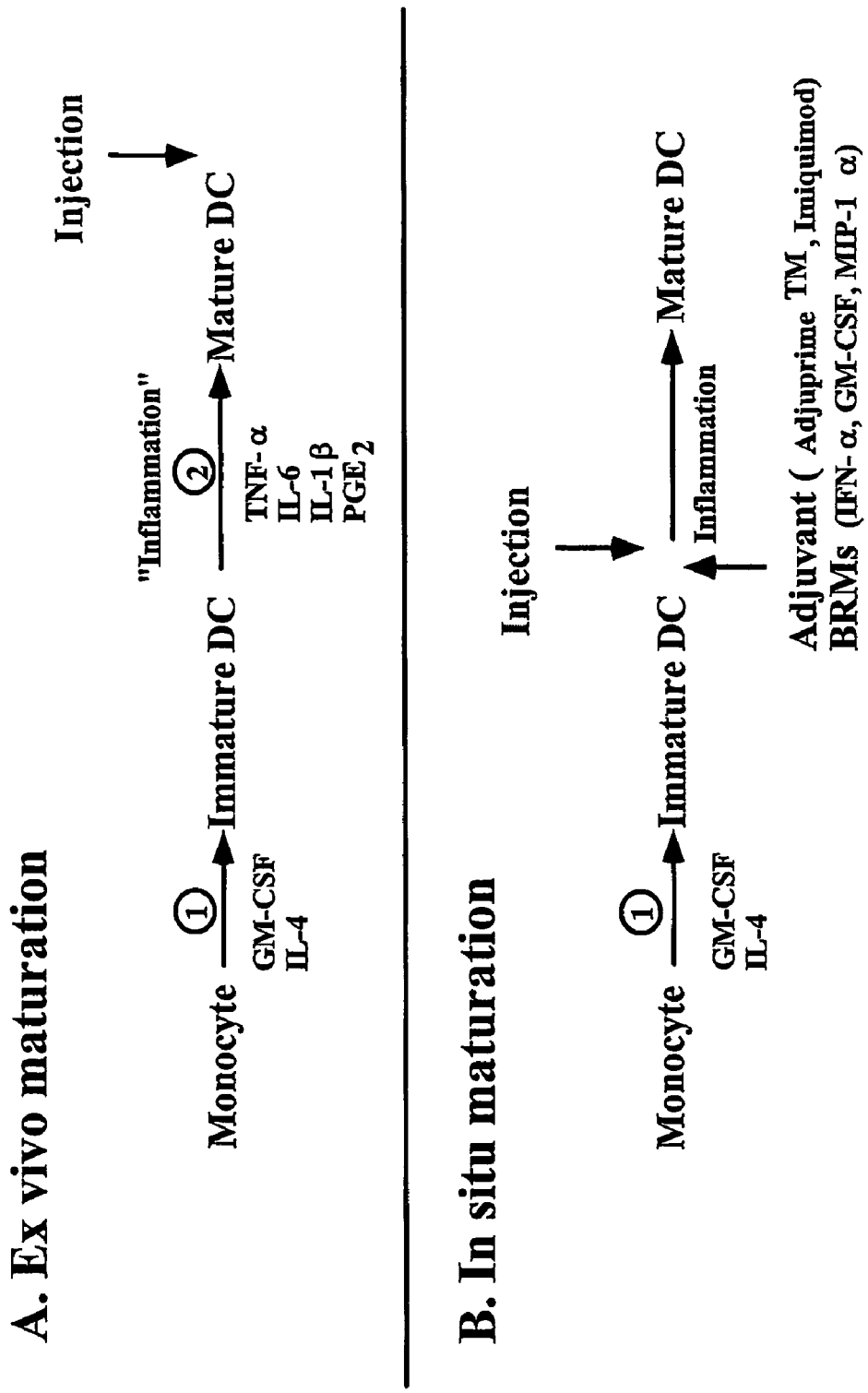
FIGS. 1A-1B are schematic diagrams that outline methods for DC maturation.

While the following terms are believed to be well understood by one of ordinary skill in the art, the following definitions are set forth to facilitate explanation of the invention.

The term "immune system" includes all the cells, tissues, systems, structures and processes, including non-specific and specific categories, that provide a defense response against cells comprising antigenic molecules, including but not limited to tumors, pathogens, and self-reactive cells. Thus, an immune response can comprise an innate immune response, an adaptive immune response, and/or a tolerizing immune response.

The term "innate immune system" includes phagocytic cells such as neutrophils, monocytes, tissue macrophages, Kupffer cells, alveolar macrophages, dendritic cells, and microglia. The innate immune system mediates non-specific immune responses. The innate immune system plays an important role in initiating and guiding responses of the adaptive immune system. See e.g., Janeway (1989) *Cold Spring Harb Symp Quant Biol* 54:1-13; Romagnani (1992) *Immunol Today* 13:379-381; Fearon & Locksley (1996) *Science* 272: 50-53; and Fearon (1997) *Nature* 388:323-324. An innate response can comprise, for example, dendritic cell maturation, macrophage activation, cytokine or chemokine secretion, and/or activation of NFκB signaling.

The term "adaptive immune system" refers to the cells and tissues that impart specific immunity within a host. Included among these cells are natural killer (NK) cells and lymphocytes (e.g., B cell lymphocytes and T cell lymphocytes). The term "adaptive immune system" also includes antibody-producing cells and the antibodies produced by the antibody-producing cells.

The term "adaptive immune response" refers to a specific response to an antigen including humoral immune responses (e.g., production of antigen-specific antibodies) and cell-mediated immune responses (e.g., lymphocyte proliferation), as defined herein below.

The terms "humoral immunity" or "humoral immune response" are meant to refer to the form of acquired immunity in which antibody molecules are secreted in response to antigenic stimulation.

The terms "cell-mediated immunity" and "cell-mediated immune response" are meant to refer to the immunological defense provided by lymphocytes, such as that defense provided by T cell lymphocytes when they come into close proximity to their target cells. A cell-mediated immune response also comprises lymphocyte proliferation in response to a specific antigen is measured. Lymphocyte proliferation is meant to refer to B cell, T-helper cell or CTL cell proliferation.

The term "CTL response" is meant to refer to the ability of an antigen-specific cell to lyse and kill a cell expressing the specific antigen. As described herein below, standard, art-recognized CTL assays are performed to measure CTL activity.

The term "tolerizing immune response" refers to a suppression of T cell activation by deletion of self-reactive thymocytes, by induction of T cell anergy, or by a combination thereof.

The terms "a," "an," and "the" are used in accordance with long-standing convention to refer to one or more.

The term "about", as used herein when referring to a measurable value, for example a number of APCs, is meant to encompass variations of in one embodiment ±20% or ±10%, in another embodiment ±5%, in another embodiment ±1%, and in yet another embodiment ±0.1% from the specified amount, as such variations are appropriate to perform a disclosed method or otherwise carry out the present invention.

II. Preparation of Antigen Presenting Cells

The methods of the present invention involve in some embodiments preparation of APCs ex vivo, followed by administration of the APCs to a subject. In one embodiment, the invention particularly provides a method for in situ maturation of APCs by administering the APCs to a subject at a pre-treated site. The disclosed methods are useful for eliciting an immune response in the subject, as described further herein below.

The term "antigen presenting cell," which is abbreviated herein as "APC," refers to a cell that processes antigens for presentation to T lymphocytes. Antigen-presenting cells, including but not limited to macrophages, monocytes, dendritic cells (for example, cutaneous epidermal Langerhans cells, dermal dendritic cells, and dendritic cells resident in lymph nodes and spleen), and B cells, can be obtained by production in vitro from stem cells and from progenitor cells found in human peripheral blood and bone marrow. See Inaba (1992) *J Exp Med* 176:1693-1702. In one embodiment, the APCs are isolated from a subject that is also the intended recipient of the APCs (autologous embodiment).

For use in the methods of the present invention, antigen presenting cells comprise in one embodiment dendritic cells, including, but not limited to Langerhans cells, follicular DCs, and lymphoid DCs. The methods of the present invention can also be used to enhance the maturation of other antigen presenting cells, including, but not limited to macrophages, monocytes, and B cells.

The term "dendritic cell" refers to an antigen presenting cell that can elicit a T cell or B cell response. Thus, the term "dendritic cell" refers to a cell expressing major histocompatability complex (MHC) molecules to which antigens are bound. Intracellular antigens are processed in the cytosol and presented on MHC class I molecules, which then activate cytotoxic T lymphocytes (CTLs). Extracellular antigens that have been endocytosed are typically presented on MHC class II molecules, which then stimulate T helper cells.

The term "Langerhans cell" refers to a type of dendritic cell that resides in the epidermal layer of the skin and mucous membranes.

The term "follicular dendritic cell" refers to a type of dendritic cell that functions to sustain the viability, growth, and differentiation of activated B cells. Follicular dendritic cells express complement receptors such as CD11b and CD35, which enable capture of antibody-antigen complexes. The captured complexes are displayed intact, rather than as peptides derived from the complexes. See Matsumoto et al. (1997) *J Exp Med* 186:1997-2004; Liu et al. (1996) *Int Rev Cytol* 166:139-179; and Liu et al. (1997) *J Exp Med* 185:165-170. CD11c+ dendritic cells can also present whole immune complexes (Grouard et al., 1996).

The term "lymphoid DC" refers to a dendritic cell that expresses a high level of MHC-self peptide complexes. See Inaba et al. (1997) *J Exp Med* 186:665-672.

As used herein, the terms "pre-treated", "pre-treat", and "pre-treatment" all refer to manipulations of a site at which an antigen presenting cell is administered to a subject that are intended to produce an environment conducive to the maturation of antigen presenting cells (e.g. dendritic cells). For example, pre-treatment can include manipulations that induce inflammation or that mimic inflammation at the site. In one embodiment, a pre-treatment comprises the administration of a biological response modifier, which includes but is not limited to an adjuvant, a vasodilator, and combinations thereof. The terms "pre-treated", "pre-treat", and "pre-treatment" can also refer to the administration of a biological response modifier (e.g. an adjuvant) to a site contemporaneously with, or prior to, administration of antigen presenting cells.

The present invention pertains in part to the belief that methods for maturation of DCs in culture (FIG. 1A) incompletely or, to a certain extent, inadequately mimic the process of DC maturation in vivo. Thus, in one embodiment of the invention, the DCs to be administered comprise immature DCs. The invention also encompasses in situ maturation of DCs that have been artificially "matured" in culture and that could lack features for optimally eliciting an immune response. See FIG. 1B.

The terms "immature dendritic cells" and "immature DCs" are used interchangeably to refer to DCs that have not matured to a state wherein they are capable of eliciting a T cell or B cell response. The term "immature DCs" also refers to DCs that are efficient at antigen capture.

The terms "mature dendritic cells" and "mature DCs" are used interchangeably to refer to immature DCs that have undergone maturation. Thus, the term "mature DCs" includes stimulating DCs, which function to induce T cell and/or B cell activation. The term "mature DCs" also encompasses tolerizing DCs, which function to suppress T cell activation by deletion of self-reactive thymocytes, by induction of T cell anergy, or by a combination thereof.

Immature and mature DCs can be identified using any one of several methods, including: (a) immunophenotypic analysis; (b) ability to migrate to a lymph node; (c) antigen capture capability; and (d) ability to present antigen and activate T cells, as described further herein below.

Immature DCs are characterized by: (a) a high level of intracellular MHC molecules, which are organized as MHC class II-rich compartments (MIICs); (b) expression of molecules that enhance antigen capture, such as the macrophage mannose receptor, DEC-205, FcR, and anti-asialoglycoprotein receptor (ASGPR) (Sallusto & Lanzavecchia, 1994; Jiang et al., 1995; Sallusto et al., 1995); (c) low or absent expression of genes encoding signals for T-cell activation such as CD40, CD54, CD80, CD86, CD25, IL-12, CD83, p55; (d) a low level of granule antigens; and (e) the presence of actin cables.

The expression of each of the above-noted molecular markers can be determined using standard immunodetection methods. For example, the MIICs are can be detected using antibodies that recognize the HLA-DM and/or H-2M proteins, which facilitate binding of peptides to MHC class molecules. Representative protocols for detecting MIICs are described by, for example, Pierre et al. (1997) *Nature* 388: 787-792; Winzler et al. (1997) *J Exp Med* 185:317-328; Sallusto & Lanzavecchia (1994) *J Exp Med* 179:1109-1118; and Nijman et al. (1995) *J Exp Med* 182:163-174, among other places.

Immature DCs are further characterized by their ability to phagocytose particles and microbes as described by Inaba et al. (1993) *J Exp Med* 178:479-488; Moll et al. (1993) *Eur J Immunol* 23:1595-1601; Reis e Sousa et al. (1993) *J Exp Med* 178:509-519; Svensson et al. (1997) *J Immunol* 158:4229-4236. Immature APCs can also sample extracellular fluid and solutes via a process called macropinocytosis (Sallusto et al., 1995). Specifically, an immature APC can capture (via phagocytosis or pinocytosis) an antigen that is present at picomolar or nanomolar concentrations.

In contrast to the above-noted features of immature DCs, mature DCs are characterized by (a) a high level of MHC class II molecules at the cell surface; (b) a low level of FcR and endocytosis; (c) expression of genes encoding signals for T-cell activation such as CD54, CD58, CD80, CD86, CD40, CD25, IL-12, CD83, p55; (d) a high level of the cytoplasmic granular antigens 2A1, M342 and MIDC-8; and (e) a heightened ability to present antigen. Methods for assaying antigen presentation on MHC class II molecules are described in, for example in Cella et al. (1997) *Nature* 388:782-787 and Pierre et al. (1997) *Nature* 388:787-792, among other places.

II.A. Antigen Presenting Cells

Antigen presenting cells employed in the methods of the present invention can be isolated from any suitable source, including stem cells (e.g., embryonic stem cells), blood monocytes, DC progenitor cells found in bone marrow, and plasmacytoid T cells.

In one embodiment of the invention, dendritic cells are prepared from blood monocytes present in the adherent fraction of blood that has been depleted of red blood cells. Blood monocytes can be isolated and cultured ex vivo in the presence of a cytokine such as GM-CSF or IL-4, to thereby prepare immature dendritic cells (Romani et al., 1994; Sallusto & Lanzavecchia, 1994).

Additional representative protocols for preparing APCs can be found in Maraskovsky et al. (1996) *J Exp Med* 184: 1953-1962; Caux et al. (1992) *Nature* 360:258-261; Inaba et al. (1992) *J Exp Med* 176:1693-1702; Szabolcs et al. (1995) *J Immunol* 154:5851-5861; Sallusto & Lanzavecchia (1994) *J Exp Med* 179:1109-1118; Romani et al. (1994) *J Exp Med* 180:83-93; Sallusto et al. (1995) *J Exp Med* 182:389-400; Grouard et al. (1997) *J Exp Med* 185:1101-1111; Reddy et al. (1997) *Blood* 90:3640-3646; U.S. Pat. Nos. 6,274,378; 6,165, 785; and 5,643,786; U.S. Patent Application Publication No. 2002/0019047; among other places.

Optionally, exogenous agents can be used to maintain DCs in an immature state prior to administration to a subject. For example, steroids can inhibit the maturation of DCs as described by Kitajima et al. (1996) *J Clin Invest* 98:142-147.

In contrast to existing strategies for DC-based therapies, which include a step of maturing DCs ex vivo (FIG. 1A), the methods of the present invention can employ immature or mature DCs (FIG. 1B). As noted herein above, in one embodiment of the invention, immature DCs are employed. However, in another embodiment, mature DCs can be used as convenient or desired for a particular purpose.

Immature DCs can be matured ex vivo using methods known in the art, for example, by culturing the immature DCs for 1-2 days in the presence of one or more maturation agents, such as CD40 ligand, LPS, and monocyte-conditioned medium. Additional representative protocols can be found, for example, in Cella et al. (1997) *Curr Opin Immunol* 9:10-16; Banchereau & Steinman (1998) *Nature* 392:245-252; Banchereau et al. (2000) *Annu Rev Immunol* 18:767-811; Bell et al. (1999) *Adv Immunol* 72:255-324; Romani et al. (1996) *J Immunol Methods* 196:137-151, Jonuleit et al. (1997) *Eur J Immunol* 27:3135-3142; and U.S. Pat. No. 5,994,126; among other places.

APCs or APC progenitor cells use in accordance with the methods of the present invention can optionally be cryopreserved prior to antigen loading and/or prior to administration to a subject at a pre-treated (for example, inflamed) site. Representative protocols can be found in, for example, U.S. Pat. Nos. 6,037,116 and 5,788,963, among other places.

II.B. Antigen Loading

The present invention pertains to APCs (e.g. DCs) that present one or more antigens to which an immune response is sought. In accordance with one embodiment of the invention, DCs are isolated from a subject, loaded with antigen ex vivo, and then re-infused into the subject.

The term "antigen" refers to a substance that induces a specific immune response when presented to immune cells of a subject. Chemically, an antigen can comprise a carbohydrate, a glycolipid, a glycoprotein, a lipid, a lipoprotein, a phospholipid, a protein, a peptide, a nucleic acid (e.g., DNA or RNA), or a combination thereof. An antigen can comprise a single immunogenic epitope, or a multiplicity of different immunogenic epitopes, for example as are present in a cell lysate, or in a complex derived therefrom.

An antigen can be derived from a pathogen (e.g., a bacterium, a virus, a fungus or a parasite), or from a cell (e.g., tumor cell or normal cell). Thus, an antigen can comprise an exogenous (non-self) antigen or a self antigen.

Antigens can be selected for use from among those known in the art or determined by immunoassay to be antigenic or immunogenic. The term "antigenic" refers to a quality of binding to an antibody or to a MHC molecule. The term "immunogenic," and grammatical equivalents thereof, refers to a quality of eliciting an immune response.

Antigenicity of a candidate antigen can be determined by various immunoassays known in the art, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in vivo immunoassays (using colloidal gold, enzyme or radioisotope labels, for example), western blots, immunoprecipitation reactions, agglutination assays (e.g., gel agglutination assays, hemagglutination assays), complement fixation assays, immunofluorescence assays, protein A assays, and immuno-electrophoresis assays.

Immunogenicity can be determined by, for example, detecting T cell-mediated responses. Representative methods for measuring T cell responses include in vitro cytotoxicity assays or in vivo delayed-type hypersensitivity assays, as described herein below. Immunogenicity can also be assessed by detection of antigen-specific antibodies in a subject's serum, and/or by a demonstration of protective effects of antisera or immune cells specific for the antigen.

Candidate immunogenic or antigenic peptides can be isolated from endogenous MHC-peptide complexes for use subsequently as antigenic molecules. The isolation of potentially immunogenic peptides from MHC molecules is well known in the art. See Falk et al. (1990) *Nature* 348:248-251; Rotzschke et al. (1990) *Nature* 348:252-254; Falk et al. (1991) *Nature* 351:290-296; Elliott et al. (1990) *Nature* 348: 195-197; Demotz et al. (1989) *Nature* 342:682-684; and Rotzschke et al. (1990) *Science* 249:283-287.

Potentially useful antigens can also be identified by various criteria, such as the antigen's involvement in neutralizing a pathogen's infectivity (wherein it is desired to treat or prevent infection by such a pathogen). See Norrby & Cold Spring Harbor Laboratory. (1994) *Vaccines 94: Modern Approaches to New Vaccines Including Prevention of Aids*. Cold Spring Harbor Laboratory Press, Plainview, N.Y.

Where it is desired to treat or prevent cancer, known tumor-specific antigens, fragments, or derivatives thereof can be used. For example, such tumor-specific or tumor-associated antigens include but are not limited to KS ¼ pan-carcinoma antigen (Bumol et al., 1988; Perez & Walker, 1989); ovarian carcinoma antigen (CA125) (Yu & Lian, 1991); prostatic acid phosphate (Tailor et al., 1990); prostate specific antigen (Henttu & Vihko, 1989; Israeli et al., 1993); melanoma-associated antigen p97 (Estin et al., 1989); melanoma antigen gp75 (Vijayasaradhi et al., 1990); high molecular weight melanoma antigen (Natali et al., 1987); and prostate specific membrane antigen (Mai et al., 2000).

Where it is desired to treat or prevent viral diseases, molecules comprising epitopes of known viruses can be used. For example, such antigenic epitopes can be prepared from viruses including any of the viruses for which a treatment is sought, as noted herein below.

Where it is desired to treat or prevent bacterial infections, molecules comprising epitopes of known bacteria can be used including, but not limited to any of the bacteria for which a treatment is sought, as noted herein below.

Where it is desired to treat or prevent protozoan or parasitic infectious, molecules comprising epitopes of known protozoa or parasites can be used. For example, such antigenic epitopes can be prepared from any protozoa or parasite, including any of those noted herein below.

Where it is desired to treat an autoimmune disease, known antigens associated with autoreactivity can be used, including, but not limited to the variable regions of autoreactive T cells and B cells. For example, the Vβ-3, Vβ-14, Vβ-17 and Vα-17 variable regions of T cell receptors are implicated in Rheumatoid arthritis (Howell et al., 1991; Paliard et al., 1991; Williams et al., 1992), the Vβ-7 and Vβ-10 variable regions of T cell receptors are implicated in multiple sclerosis (Oksenberg et al., 1990; Wucherpfennig et al., 1990), and the Vβ-6, Vβ-8, Vβ-14 and Vα-16, Vα-3C, Vα-7, Vα-14, Vα-15, Vα-16, Vα-28 and Vα-12 variable regions of T cell receptors are implicated in scleroderma.

A purified antigen can be obtained by a recombinant approach, by chemical synthesis, or by purification from a natural source. An antigen can also comprise a whole organism (e.g., a bacterium, a live virus, an attenuated live virus, or an inactivated virus), or an extract or lysate prepared therefrom.

Methods for antigen loading onto dendritic cells are known in the art. Where it is desirable for DCs to take up antigen by phagocytosis, antigen can be added to the cultures of immature DCs. For example, phagocytosis is useful for loading of DCs with particulate antigens or immune complexes.

Soluble peptide antigens can be similarly administered to immature or mature DCs. In a representative method for antigen loading, approximately $1 \times 10^6$ to $5 \times 10^6$ DCs are exposed to antigen at a concentration of between about 10 pM to about 10 μM. In one embodiment, about 1 μM antigen is exposed to about 3 million DCs. The DCs are cultured in the presence of the antigen for a sufficient time to allow for uptake and presentation. Typically uptake and processing can occur within 24 hours but longer (up to and including 4 days) or shorter (about 1-2 hours) periods may also be used.

Antigen loading onto DCs can also be accomplished by washing endogenous peptide fragments off of the surface of a DC (e.g., in a mildly acidic or detergent containing wash) and then applying peptide fragments to the surface of the cell, for example as described by Tsai et al. (1997) *J Immunol* 158: 1796-1802.

Peptide or protein antigens can also be delivered to DCs using commonly known pulsing methods, for example as described by Nestle et al. (1998) *Nat Med* 4:328-332 and by Tsai et al. (1997) *J Immunol* 158:1796-1802.

For many applications, proteins or peptides comprising antigens can be expressed in DCs or DC progenitors using recombinant DNA technology. General texts that describe molecular biological techniques relevant to the recombinant expression of an antigen include Sambrook et al. (eds.) (1989) *Molecular Cloning: A Laboratory Manual*. Cold Spring Harbor Laboratory Press, Cold Spring Harbor, N.Y., United States of America; Silhavy et al. (1984) *Experiments with Gene Fusions*. Cold Spring Harbor Laboratory, Cold Spring Harbor, N.Y., United States of America; Glover & Hames (1995) *DNA Cloning: A Practical Approach*, 2nd ed. IRL Press at Oxford University Press, Oxford/New York; and Ausubel (ed.) (1995) *Short Protocols in Molecular Biology*, 3rd ed. Wiley, New York.

Antigen presenting cells can also be loaded with RNA derived from cells to which an immune response is sought, such as tumors and pathogens. Such RNA can be loaded into APCs using conventional nucleic acid transfection methods, such as lipid-mediated transfection, electroporation, and calcium phosphate transfection. See Nair et al. (1998) *Nat Biotechnol* 16:364-369 and U.S. Pat. Nos. 6,306,388 and 5,853,719.

III. In Situ Maturation of Antigen Presenting Cells

DCs are located in most tissues, where they capture and process antigens for display as MHC-peptide complexes on their cell surface. Following antigen capture, DCs upregulate their co-stimulatory molecules and migrate to lymphoid organs, e.g. the spleen and the lymph nodes, where they can activate or tolerize T cells.

The induction of dendritic cell migration is a complex process that is incompletely understood. Several signals have been identified that function to mobilize or induce the migration of immature dendritic cells from their place of residence, including GM-CSF, TNF-α, IL-1, MIP-1α, MIP-1β, and LPS (Banchereau & Steinman, 1998; Kimber et al., 2000). Immature DCs mature while en route to the lymph nodes, and these same signals also trigger DC maturation. Physical trauma to a tissue, for example a surgical excision, can also induce the migration and maturation of resident immature dendritic cells (Steinman et al., 1995).

As provided herein, in some embodiments, antigen-loaded DCs can be administered to a subject at a pre-treated site, whereby the DCs are induced to mature and migrate to lymphoid organs. In particular, the pre-treatment of the site produces an environment that induces in situ maturation of the administered DCs. See FIG. 1B.

III.A. Inflammation

The terms "inflammation" and "inflamed" are used herein to broadly describe any tissue condition in which an environment conducive to the maturation of antigen presenting cells (e.g. dendritic cells) is produced locally. For example, an inflammation response can be observed in response to injury and/or challenge. An injury that elicits an inflammatory response can comprise an infection, exposure to a chemical agent or adjuvant, or physical disruption. An inflammation is typically characterized by pain, heat, redness, and swelling of the affected tissue. One of the consequences of inflammation is that antigen presenting cells within the area of inflammation are induced to mature. In a representative embodiment of the invention, a site is pre-treated with a biological response modifier, whereby a site of inflammation and/or inflammation-like conditions is generated, followed by administration of DCs at the pre-treated site. By "administration of the antigen presenting cells (e.g. DCs) at the pre-treated site" it is meant to include such administration directly at the site of administration of the biological response modulator, such administration immediately adjacent to the site of administration of the biological response modifier, any other such administration so long as the antigen presenting cells are in an in situ environment conducive to the maturation of the antigen presenting cells, and combinations thereof.

The term "biological response modifier" generally refers to an agent that contributes to the provisions of an environment conducive to the maturation of antigen presenting cells. In some embodiments, the biological response modifier comprises an agent that induces or potentiates an immune response; and in some embodiments, the biological response modifier comprises an agent that suppresses or inhibits an immune response. The immune response can comprise a specific or non-specific immune response. Biological response modifiers include, but are not limited to adjuvants, vasodilators, and cytokines. In one embodiment, a biological response modifier is an adjuvant. In some embodiments of the presently disclosed methods, an adjuvant is used to induce an immune response comprising inflammation. See FIG. 1B.

Representative adjuvants include, for example, an oil emulsion (e.g., complete or incomplete Freund's adjuvant), a chemokine (e.g., defensin 1, defensin 2, RANTES, MIP1-α, MIP-2, interleukin-8), a cytokine (e.g., IL-1β, IL-2, IL-6, IL-10 and IL-12; γ-interferon; TNF-α; and GMC-SF) (Nohria & Rubin, 1994), a muramyl dipeptide derivative (e.g., murabutide, threonyl-muramyl dipeptide or muramyl tripeptide), a heat shock protein, a derivative of *Leishmania major* LeIF (Skeiky et al., 1995), cholera toxin or cholera toxin B (e.g., Ribi adjuvant, available from Universal Biologicals Limited or Gloucestershire, ENGLAND), a lipopolysaccharide (LPS) or derivative thereof (e.g., lipid A or monophosphoryl lipid A), alum preparations (e.g., aluminum phosphate, aluminum hydroxide, and thimerosal), a saponin (e.g., QS21 and GPI-0100) (U.S. Pat. Nos. 5,977,081 and 6,080,725), and a superantigen (Saloga et al., 1996). See also Richards (1995) In Powell, M. F., Newman, M. J. and Burdman, J. R. (eds.), *Vaccine Design: The Subunit and Adjuvant Approach*. Plenum Press, New York, pp. xliv, 949. In one embodiment, the methods of the present invention employ a Th1-inducing adjuvant. In another embodiment, the methods of the present invention employ a Th2-inducing adjuvant.

The time at which a biological response modifier (e.g. an adjuvant) can be administered to a site to induce or potentiate an immune response can vary. For example a biological response modifier (e.g. an adjuvant) is administered to a site contemporaneously with, or prior to, administration of antigen presenting cells. In one embodiment, an adjuvant is administered to a site between 0 and 15 minutes before antigen presenting cells are administered to the site. Reference to "0" can refer to contemporaneous or immediate administration of the adjuvant with the antigen presenting cells. For example, an adjuvant can be administered to a site 0, 5, 10, or 15 minutes before antigen presenting cells. In another embodiment, an adjuvant is administered to a site between 15 and 60 minutes before antigen presenting cells are administered to the site. For example, an adjuvant can be administered to a site 20, 25, 30, 35, 40, 45, 50, 55, or 60 minutes before the antigen presenting cells. In another embodiment, an adjuvant is administered to a site between 1 and 3 hours before the antigen presenting cells are administered to the site. For example, an adjuvant can be administered 1, 1.25, 1.5, 2, 2.25, 2.5, 2.75, or 3 hours before the antigen presenting cells are administered to the site. In another embodiment, an adjuvant is administered to a site between 3 and 5 hours before antigen presenting cells are administered to the site. For example, an adjuvant can be administered 3, 3.25, 3.5, 3.75, 4, 4.25, 4.5, 4.75, or 5 hours before antigen presenting cells are administered to the site. In another embodiment, an adjuvant is administered to a site between 5 and 8 hours before the antigen presenting cells are administered to the site. For example, an adjuvant can be administered 5, 5.25, 5.5, 5.75, 6, 6.25, 6.5, 6.75, 7, 7.25, 7.5, 7.75, or 8 hours before antigen presenting cells are administered to the site. In yet another embodiment, an adjuvant is administered to a site more than 8 hours before the antigen presenting cells are administered to the site. For example, an adjuvant can be administered 8, 8.5, 9, 9.5, 10, 10.5, 11, 11.5, or 12 hours or more before the antigen presenting cells are administered to the site.

Optionally, a vasodilator can be co-administered with an adjuvant to facilitate the inflammatory response by promoting blood flow to the treatment area. For example, the neuropeptide vasoactive intestinal peptide (VIP) synergizes with TNF-α to promote DC maturation (Delneste et al., 1999). Additional representative vasodilators include reserpine, hydralazine, nitroglycerin, isosorbide dinitrate, and nitric oxide.

In accordance with the methods of the present invention, adjuvants can be selected to control the type of the immune response generated by DCs administered at an adjuvant-induced inflammation. Thus, an adjuvant can be chosen to preferentially induce antibody or cellular effectors, including specific antibody isotypes (e.g., IgM, IgD, IgA1, IgA2, secretory IgA, IgE, IgG1, IgG2, IgG3, and/or IgG4) and specific T-cell subsets (e.g., CTL, Th1, Th2 and/or $T_{DTH}$). Alternatively, an adjuvant can be selected to suppress an immune response, for example, to induce T cell tolerance.

For example, IL-12 directs T helper 1 (Th1) differentiation (Hsieh et al., 1993; Manetti et al., 1993), IL-4 mediates Th2 cell differentiation (Le Gros et al., 1990; Swain et al., 1990; Shimoda et al., 1996; and U.S. Patent Application Publication No. 2001/0026937), and TGF-β favors differentiation of Th3 cells (Chen et al., 1994). IL-10 has been shown to skew T cell responses toward T regulatory cells that inhibit antigen-specific T cell responses (Groux et al., 1997; Asseman et al., 1999). Additional methods for eliciting a tolerizing immune response include strategies for promoting APC maturation while preventing CD4+ T cell help as described in U.S. Patent Application Publication No. 2002/0004041. For example, CD4+ T cell help can be blocked using FK506 or rapamycin.

As described further herein below, the present invention can be used to treat cancer via pre-treatment with an adjuvant that elicits inflammation and promotes Th1 responses, followed by administration of DCs bearing cancer antigens at the pre-treated site. To promote a humoral immune response, for example for the treatment of infectious disease, DCs can be administered at a site previously treated with an adjuvant that promotes a Th2 response. To treat autoimmune disease or improve transplantation integration, a site of inflammation can be created using an adjuvant that promotes differentiation of DCs into tolerizing DCs.

A biological response modifier (e.g. an adjuvant) can be formulated as appropriate for administration via combination with a pharmaceutically acceptable carrier. Additionally, a biological response modifier (e.g. an adjuvant) can be formulated with antigen presenting cells to provide a composition that can be used to provide contemporaneous administration of biological response modifier and antigen presenting cells, in some embodiments of the presently disclosed methods. Suitable formulations include aqueous and non-aqueous sterile injection solutions, which can contain anti-oxidants, buffers, bacteriostats, bactericidal antibiotics, solutes to render the formulation isotonic with the bodily fluids of the intended recipient, detergents, suspending agents, and thickening agents. The formulations, including formulations comprising biological response modifier (e.g. adjuvant) and antigen presenting cells (e.g. dendritic cells) can be presented in unit-dose or multi-dose containers, for example sealed ampoules, vials or patches, and can be stored in a frozen or freeze-dried (lyophilized) condition requiring only the addition of sterile liquid carrier, for example water for injections, immediately prior to use.

A formulated adjuvant can comprise a cream, an emulsion, a gel, a lotion, an ointment, a paste, a solution, a suspension, or any other form known in the art. A formulated adjuvant can also comprise other pharmaceutically acceptable additives including, for example, diluents, stabilizing agents, preservatives, and colorings.

To create a pre-treated site, a biological response modifier (e.g. an adjuvant) can be administered to a subject via any suitable approach, including but not limited to subcutaneous injection, intramuscular injection, or transcutaneous delivery (U.S. Pat. Nos. 5,910,306 and 5,980,898).

In a representative embodiment of the invention, an inflammation is induced at a cutaneous site, at which DCs are contemporaneously and/or thereafter administered. A cutaneous site can comprise a location superficial to a draining lymph node field. The term "draining lymph node field" as used in the invention means an anatomic area over which the lymph collected is filtered through a set of defined set of lymph nodes (e.g., a cervical lymph node field, an axillary lymph node field, and inguinal lymph node field, an epitrochelear lymph node field, a popliteal lymph node field, and a lymph node of the abdomen and thorax).

III.B. Administration of Antigen Presenting Cells

APCs (e.g. antigen-loaded DCs) are preferably administered to a subject locally, such as by intradermal, intramuscular, or subcutaneous injection. For example, antigen-loaded DCs are administered to the same subject from whom they were isolated (autologous therapy).

Preferably, a therapeutically effective amount of DCs is administered to a subject. A "therapeutically effective amount" refers to a number or volume of DCs sufficient to produce a measurable immune response. A person of skill in the art will be able to choose an appropriate dosage, e.g. the number and concentration of cells, to take into account the fact that only a limited volume of fluid can be administered in this manner. Subjects typically receive from about $10^5$ to about $10^{12}$ DCs, which are administered in a physiologically compatible carrier.

Actual dosage levels can be varied so as to administer an amount of DCs that is effective to achieve the desired therapeutic response for a particular subject and condition. The selected dosage level will depend upon a variety of factors including the immune response sought, features of the pre-treated site, the route of administration, combination with other drugs or treatments, and the physical condition and prior medical history of the subject being treated. Determination and adjustment of a therapeutically effective dose, as well as evaluation of when and how to make such adjustments, can be determined by one of ordinary skill in the art of medicine upon a review of the disclosure herein.

Optionally, the disclosed methods for promoting in situ maturation of DCs can further comprise administering a treatment for promoting DC cell migration, for example provision of dibutylphthalate or low frequency ultrasound as described in U.S. Pat. No. 6,210,672 and U.S. Patent Application Publication No. 2001/0024649. A supplementary treatment can also include administration of a chemokine for recruiting DCs to lymphoid organs. For example, 6Ckine, MIP-3β and MIP-3α function as chemoattractants to promote the egress of DCs from skin (PCT International Publication Nos. WO 00/09151 and WO 00/46248).

IV. Applications

The methods of the present invention can be used to enhance the immunocompetence of a subject via eliciting an immune response against antigens associated with diseases and disorders such as allergy, infection, cancer, and any other immunodeficiency. The methods of the present invention can also be used to suppress an immune response, for example to minimize transplant rejection and to treat autoimmune disease. The present invention further pertains to the administration and in situ maturation of DCs to a subject at risk of developing any of the foregoing diseases and disorders due to familial history or environmental factors. Thus, the disclosed methods can be used to prevent the onset of a disease or condition, or to reduce the severity and/or duration of an existing disease or condition.

IV.A. Treatment of Cancer and Other Proliferative Disorders

The present invention provides a method for inhibiting cancer growth via administration and in situ maturation of DCs bearing a cancer antigen, to thereby induce anti-cancer immune response.

The term "cancer" as used herein generally refers to tumors, neoplastic cells and preneoplastic cells, and other disorders of cellular proliferation.

The term "tumor" encompasses both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). The term "tumor" also encompasses solid tumors arising from hematopoietic malignancies such as leukemias, including chloromas, plasmacytomas, plaques and tumors of mycosis fungoides and cutaneous T-cell lymphoma/leukemia, and lymphomas including both Hodgkin's and non-Hodgkin's lymphomas.

The term "neoplastic cell" refers to new and abnormal cell. The term "neoplasm" encompasses a tumor.

The term "preneoplastic" cell refers to a cell that is in transition from a normal to a neoplastic form.

The compositions of the present invention can also be use for the treatment or prevention of non-neoplastic cell growth such as hyperplasia, metaplasia, and dysplasia. See Kumar et al. (1997) *Basic Pathology*, 6th ed. W.B. Saunders Co., Philadelphia, Pa., United States of America.

The term "hyperplasia" refers to an abnormal cell proliferation involving an increase in cell number in a tissue or organ, without significant alteration in structure or function. As one example, endometrial hyperplasia often precedes endometrial cancer.

The term "metaplasia" refers to abnormal cell growth in which one type of adult or fully differentiated cell substitutes for another type of adult cell. Metaplasia can occur in epithelial or connective tissue cells. Atypical metaplasia can result in a disordered metaplastic epithelium.

The term "dysplasia" refers to abnormal cell proliferation involving a loss in individual cell uniformity and in the architectural orientation of cells. Dysplastic cells often have abnormally large, deeply stained nuclei, and exhibit pleomorphism. Dysplasia is frequently a forerunner of cancer, and is found mainly in the epithelia of irritated or inflamed tissues, including the cervix, respiratory passages, oral cavity, and gall bladder.

The methods of the present invention can be combined with conventional cancer therapies. For example, administration of composition of the present invention can be used to minimize infection and other complications resulting from immunosuppression. The therapeutic methods disclosed herein are also useful for controlling metastases, for example metastases arising from tumor cells shed into the circulation during surgical removal of a tumor.

The term "cancer growth" generally refers to any one of a number of indices that suggest change within the cancer to a more developed form. Thus, indices for measuring an inhibition of cancer growth include but are not limited to a decrease in cancer cell survival, a decrease in tumor volume or morphology (for example, as determined using computed tomographic (CT), sonography, or other imaging method), a delayed tumor growth, a destruction of tumor vasculature, improved performance in delayed hypersensitivity skin test, an increase in the activity of cytolytic T-lymphocytes, and a decrease in levels of tumor-specific antigens.

The term "delayed tumor growth" refers to a decrease in a duration of time required for a tumor to grow a specified amount. For example, treatment can delay the time required for a tumor to increase in volume 3-fold relative to an initial day of measurement (day 0) or the time required to grow to 1 $cm^3$.

IV.B. Treatment of Infection

The methods of the present invention can also be used to enhance an immune response against cells infected with an antigen. Thus, the present invention provides a method for eliciting an immune response in a subject, wherein the immune response comprises an anti-pathogen response, via administration of DCs at a pre-treated site.

The term "pathogen" and "infectious agent" are used interchangeably herein to refer to a bacterium, a virus, a fungus, a protozoan, a parasite, other infective agent, or potentially harmful or parasitic organism. Normal microbial flora are also potential pathogens.

Representative bacterial infectious that can be treated or prevented using the methods of the present invention include but are not limited to those infections caused by species of the genera *Salmonella, Shigella, Actinobacillus, Porphyromonas, Staphylococcus, Bordetella, Yersinia, Haemophilus, Streptococcus, Chlamydophila, Alliococcus, Campylobacter, Actinomyces, Neisseria, Chlamydia, Treponema, Ureaplasma, Mycoplasma, Mycobacterium, Bartonella, Legionella, Ehrlichia, Escherichia, Listeria, Vibrio, Clostridium, Tropheryma, Actinomadura, Nocardia, Streptomyces*, and *Spirochaeta*.

Representative viral infections that can be treated or prevented by the methods of the present invention include but are not limited to those infections caused by DNA viruses, such as Poxviridae, Herpesviridae, Adenoviridae, Papoviridae, Hepadnaviridae, and Parvoviridae. RNA viruses are also envisioned to be detected in accordance with the disclosed methods, including Paramyxoviridae, Orthomyxoviridae, Coronaviridae, Arenaviridae, Retroviridae, Reoviridae, Picornaviridae, Caliciviridae, Rhabdoviridae, Togaviridae, Flaviviridae, and Bunyaviridae.

Representative viruses include but are not limited to, hepatitis viruses, flaviviruses, gastroenteritis viruses, hantaviruses, Lassa virus, Lyssavirus, picornaviruses, polioviruses, enteroviruses, nonpolio enteroviruses, rhinoviruses, astroviruses, rubella virus, HIV-1 (human immunodeficiency virus type 1), HIV-2 (human immunodeficiency virus type 2), HTLV-1 (human T-lymphotropic virus type 1), HTLV-2 (human T-lymphotropic virus type 2), HSV-1 (herpes simplex virus type 1), HSV-2 (herpes simplex virus type 2), VZV (varicellar-zoster virus), CMV (cytomegalovirus), HHV-6 (human herpes virus type 6), HHV-7 (human herpes virus type 7), EBV (Epstein-Barr virus), influenza A and B viruses, adenoviruses, RSV (respiratory syncytial virus), PIV-1 (parainfluenza virus, types 1, 2, and 3), papillomavirus, JC virus, polyomaviruses, BK virus, filoviruses, coltiviruses, orbiviruses, orthoreoviruses, retroviruses, and spumaviruses.

Representative fungal infections that can be treated or prevented using the methods of the present invention include but are not limited to those infections caused by species of the genera *Aspergillus, Trichophyton, Microsporum, Epidermaophyton, Candida, Malassezia, Pityrosporum, Trichosporon, Exophiala, Cladosporium, Hendersonula, Scytalidium, Piedraia, Scopulariopsis, Acremonium, Fusarium, Curvularia, Penicillium, Absidia, Pseudallescheria, Rhizopus, Cryptococcus, MuCunninghamella, Rhizomucor, Saksenaea, Blastomyces, Coccidioides, Histoplasma, Paraoccidioides, Phialophora, Fonsecaea, Rhinocladiella, Conidiobolu, Loboa, Leptosphaeria, Madurella, Neotestudina, Pyrenochaeta, Colletotrichum, Alternaria, Bipolaris, Exserohilum, Phialophora, Xylohypha, Scedosporium, Rhinosporidium*, and *Sporothrix*.

Protozoal infections that can be treated or prevented by the methods of the present invention include but are not limited to those infections caused by species of the genera *Toxoplasma, Giardia, Cryptosporidium, Trichomonas*, and *Leishmania*. Other infections that can be treated or prevented by the methods of the present invention include but are not limited to those infections caused by parasitic species of the genera *Rickettsiae* and by nematodes such as species of the genera *Trichinella* and *Anisakis*.

IV.C. Autoimmune Disease

The methods of the present invention can also be used to treat individuals suffering from autoimmune diseases and disorders, which involve a self-directed immune response. For example, the disclosed methods can be used to elicit an immune response against autoreactive immune cells.

Representative T cell-mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Administration and in situ maturation of DCs expressing the variable region of the autoreactive T cells can be used to elicit an immune response to eliminate autoreactive T cells.

Representative B cell-mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies that bind to endogenous antigens and initiate an immune response. Administration and in situ maturation of APCs expressing an antigen comprising the variable region of the B cells can be used to elicit an immune response to eliminate autoreactive B cells.

In addition to the above-mentioned strategies for elimination of autoreactive immune cells, autoimmune disease can also be treated via immunosuppression approaches as described herein below.

IV.D. Immunosuppression

The methods of the present invention can also be used to elicit immune tolerance, wherein an antigen-specific immune response is prevented or minimized.

For example, immunosuppressive methods can be used to obviate an immune response to foreign antigens following transplantation. Transplant antigens include those donor antigens that are allogeneic or xenogeneic to the transplant recipient and that are prone to immune attack. The methods of the present invention can be used to tolerize the host subject prior to or during transplantation to thereby prevent, delay or treat active graft rejection.

Immunosuppressive methods can be used similarly for the treatment of autoimmune conditions. Self antigens to which tolerance is important include all antigens targeted during autoimmune disease, including but not limited to those listed herein above.

IV.E. Monitoring Immune Response

Methods for monitoring an immune response in a subject are known to one skilled in the art. Representative methods that can be used as general indicators of an immune response are described herein below. Additional methods suitable for assessment of particular therapies or applications can also be used.

Delayed Hypersensitivity Skin Test. Delayed hypersensitivity skin tests are of great value in the overall immunocompetence and cellular immunity to an antigen. Inability to react to a battery of common skin antigens is termed anergy (Sato et al., 1995). Proper technique of skin testing requires that the antigens be stored sterile at 4° C., protected from light and reconstituted shortly before use. A 25-gauge or 27-gauge needle ensures intradermal, rather than subcutaneous, administration of an antigen. Twenty-four and forty-eight hours after intradermal administration of the antigen, the largest dimensions of both erythema and induration are measured with a ruler. Hypoactivity to any given antigen or group of antigens is confirmed by testing with higher concentrations of antigen or, in ambiguous circumstances, by a repeat test with an intermediate concentration.

Activity of Cytolytic T-lymphocytes In Vitro. $8\times10^6$ peripheral blood derived T lymphocytes isolated by the Ficoll-Hypaque centrifugation gradient technique, are re-stimulated with $4\times10^4$ mitomycin C treated tumor cells in 3 ml RPMI medium containing 10% fetal calf serum. In some experiments, 33% secondary mixed lymphocyte culture supernatant or IL-2, is included in the culture medium as a source of T cell growth factors.

To measure the primary response of cytolytic T-lymphocytes after immunization, T cells are cultured without the stimulator tumor cells. In other experiments, T cells are re-stimulated with antigenically distinct cells. After six days, the cultures are tested for cytotoxicity during a period of about 4 hours using $^{51}$Cr-release assay. The spontaneous $^{51}$Cr-release of the targets preferably reaches a level less than 20%. To determine anti-MHC class I blocking activity, a ten-fold concentrated supernatant of W6/32 hybridoma is added to the test at a final concentration of about 12.5% (Heike et al., 1994).

Levels of Cell-Specific Antigens. Monitoring of disease and infection can also be accomplished using any one of a variety of biochemical techniques that assay a level of antigen whose presence is indicative of disease or infection.

For example, carcinoembryonic antigen (CEA) is a glycoprotein found on human colon cancer cells, but not on normal adult colon cells. Subjects with other tumors, such as pancreatic and breast cancer, also have elevated serum levels of CEA. Therefore, monitoring the fall and rise of CEA levels in cancer patients undergoing therapy has proven useful for predicting tumor progression and responses to treatment. Similarly, serum levels of prostate-specific antigen (PSA) are indicative of a risk for developing prostrate cancer.

Immunodiagnostic methods can be used to detect antigens present on pathogens present in infected cells. For example, a pathogen-specific antigen can comprise a polypeptide that mediates disease progression, i.e. toxic shock syndrome toxin-1 or an enterotoxin.

Gene Expression. Disease and infection can also be monitored by detection of a nucleic acid presence or amount that is characteristic to disease or infection. Formats for assaying gene expression can include but are not limited to PCR amplification of a target nucleic acid and hybridization-based methods of nucleic acid detection. These assays can detect the presence and/or level of a single target nucleic acid or multiple target nucleic acids, for example by microarray analysis.

Target-specific probes can be designed according to nucleotide sequences in public sequence repositories (e.g., Sanger Centre (ftp://ftp.sanger.ac.uk/pub/tb/sequences) and GenBank (http://ncbi.nlm.nih.gov)), including cDNAs, expressed sequence tags (ESTs), sequence tagged sites (STSs), repetitive sequences, and genomic sequences.

Representative methods for detection of nucleic acids and the selection of appropriate target genes are described in, for example, Quinn (1997) in Lee et al., eds., *Nucleic Acid Amplification Technologies: Application to Disease Diagnostics*, pp. 49-60, Birkhäuser Boston, Cambridge, Mass., United States of America; Richardson & Warnock (1993) *Fungal Infection: Diagnosis and Management*, Blackwell Scientific Publications Inc., Boston, Mass., United States of America; Storch (2000) *Essentials of Diagnostic Virology*, Churchill Livingstone, New York, N.Y.; Fisher & Cook (1998) *Fundamentals of Diagnostic Mycology*, W.B. Saunders Company, Philadelphia, Pa., United States of America; White & Fenner (1994) *Medical Virology*, 4$^{th}$ Edition, Academic Press, San Diego, Calif., United States of America; and Schena (2000) *Microarray Biochip Technology*. Eaton Publishing, Natick, Mass., United States of America.

IV.E. Subjects

With respect to the therapeutic methods of the present invention, a preferred subject is a vertebrate subject. A preferred vertebrate is warm-blooded; a preferred warm-blooded vertebrate is a mammal. A preferred mammal is a mouse or, most preferably, a human. As used herein and in the claims, the term "subject" includes both human and animal subjects. Thus, veterinary therapeutic uses are provided in accordance with the present invention.

Also provided is the treatment of mammals such as humans, as well as those mammals of importance due to being endangered, such as Siberian tigers; of economical importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, provided is the treatment of livestock, including, but not limited to, domesticated swine, ruminants, ungulates, horses (including race horses), poultry, and the like.

EXAMPLES

The following Examples have been included to illustrate preferred modes of the invention. Certain aspects of the following Examples are described in terms of techniques and procedures found or contemplated by the present inventors to work well in the practice of the invention. These Examples are exemplified through the use of standard practices of the inventors. In light of the present disclosure and the general level of skill in the art, those of skill will appreciate that the following Examples are intended to be exemplary only and that numerous changes, modifications, and alterations can be employed without departing from the spirit and scope of the invention.

Example 1

Procedure for DC Generation

Marrow from tibias and femurs of C57BL/6 mice were harvested followed by treatment of the precursors with ammonium chloride Tris buffer for 3 min at 37° C. to deplete the red blood cells. The precursors were plated in RPMI-5% FCS with GM-CSF (15 ng/ml) and IL-4 (10 ng/ml). GM-CSF-containing supernatant was harvested after 24 h capillary culture from GM-CSF producing melanoma cell line (F10.9/GM-CSF) and IL-4 was obtained from Peprotech (Rocky Hill, N.J., United States of America). The concentration of GM-CSF used was determined by ELISA. Cells were plated at 106/ml and incubated at 37° C. and 5% $CO_2$. Three days later the floating cells (mostly granulocytes) were removed and the adherent cells replenished with fresh GM-CSF and IL-4 containing medium. For immature dendritic cells, non-adherent cells were harvested on day 5, electroporated or untreated and replated at 106/ml in GM-CSF and IL-4 containing medium. For mature dendritic cells, non-adherent cells were harvested on day 7 (as per standard protocol for generating murine DC), washed and replated at 106/ml in GM-CSF and IL-4 containing medium. After 1 day (day 8 DC) the non-adherent cells were harvested, washed and electroporated with RNA or just replated with no electroporation. The day 9 DC were harvested as mature dendritic cells. For migration studies, untreated day 6 and day 9 DC were washed and labeled with 1 μM 5,6-carboxy-succinimidyl-fluoresceine-ester (CSFE; Molecular Probes, Inc., Eugene, Oreg., United States of America), per manufacturer's protocol.

Example 2

Immunophenotype of Murine Bone Marrow Derived DC

Immature DC were generated from the bone marrow of mice by a 6 day culture in the presence of GM-CSF and IL-4 using established protocols (see Inaba et al., *J Exp Med* 176: 1693-702, 1992) with slight modifications (see Mitchell et al., *Eur J Immunol* 28:1923-33, 1998; published erratum appears in *Eur J Immunol* 28:3891, 1998) and either loaded with mRNA encoding the chicken ovalbumin (OVA) model antigen or replated and allowed to grow for another 24 hours after which the non adherent cells, the mature DC, were collected, and transfected with OVA mRNA. RNA transfections were carried out by electroporation. See e.g., Van Tendeloo et al., *Blood* 98:49-56, 2001; Saeboe-Larssen et al., *J Immunol Methods* 259:191-203, 2002. Antigen loaded immature or mature DC were injected into the ear pinna and mice were evaluated for (a) migration of the DC to the draining auricular lymph node or (b) induction of OVA CTL.

Immature DC were injected into either untreated skin or skin pretreated with ADJUPRIME™ adjuvant (thought to stimulate Th1 immunity and available from Pierce Biotechnology, Inc., Rockford, Ill., United States of America). To monitor migration of DC to the lymph node, prior to injection the DC were stained with carboxyfluoroscein succinimidyl ester (CFSE). Twenty-four hours post injection the draining auricular lymph node was dissected and cell suspension generated using a published protocol that preserves the integrity of the dendritic cell population. See Vremec & Shortman, *J Immunol* 159:565-73, 1997. Cells were analyzed by flow cytometry as shown in FIG. 2.

Figure 2:
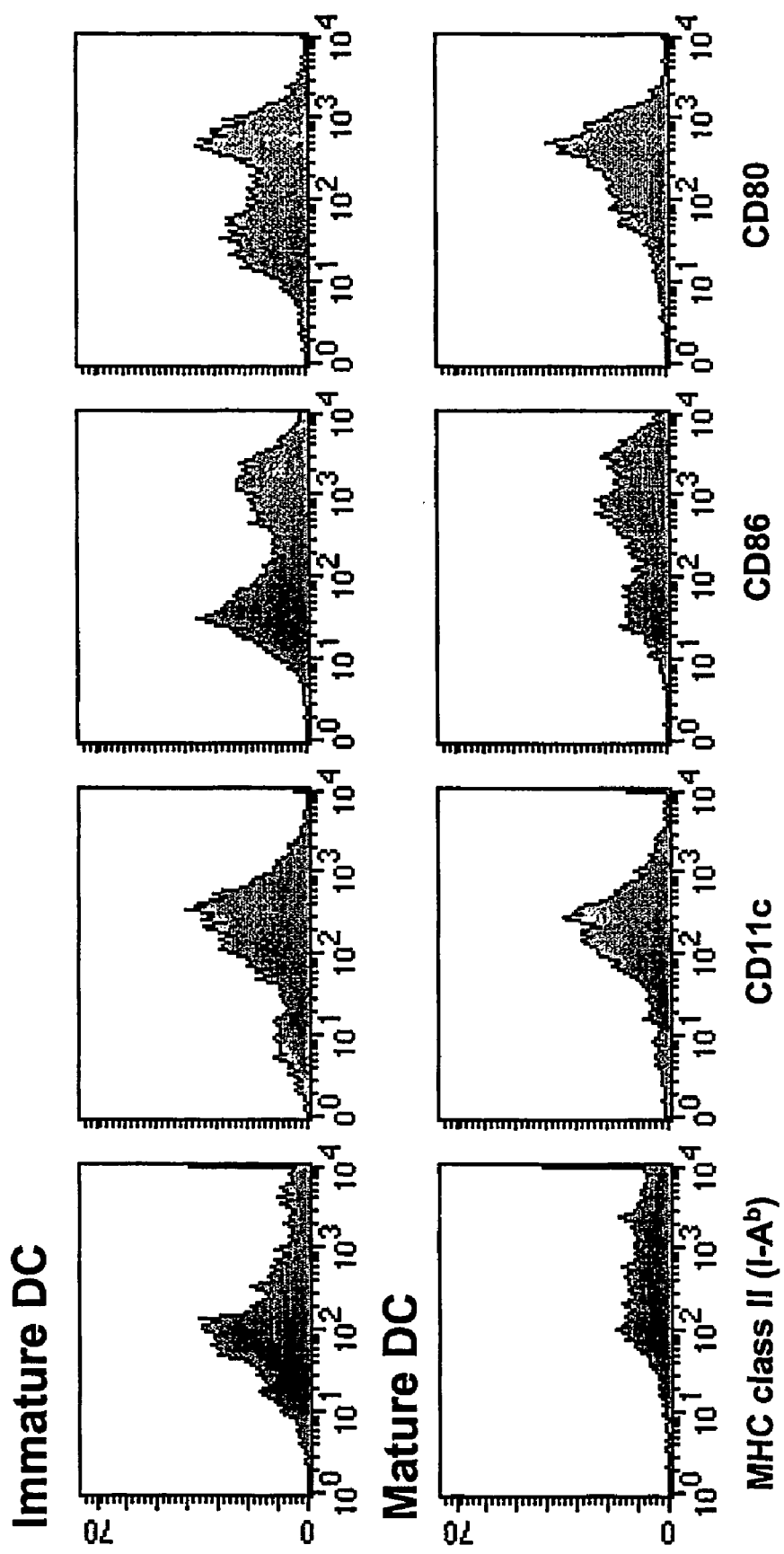
FIG. 2 depicts flow cytometry analysis of the immunophenotype of murine bone marrow derived DC. DC were generated from the bone marrow of C75BL/6 mice according to established procedures. See Inaba et al., *J Exp Med* 176:1693-702, 1992, and the modifications found in Mitchell et al., *Eur J Immunol* 28:1923-33, 1998 (published erratum appears in *Eur J Immunol* 28:3891, 1998). Immature DC were obtained after a 6-day culture period in the presence of GM-CSF and IL-4. Mature DC were generated by replating the immature DC and allowing them to grow for 24 hours before collecting the non-adherent cells. Cells were stained with FITC-labeled antibodies as indicated and analyzed by flow cytometry.

FIG. 2 shows the cell surface phenotype of the immature and mature DC populations used in these studies. The day 6 DC culture exhibit typical immature phenotype, notably reduced expression of class II and B7-1 on the cell surface. By contrast, the mature DC upregulate the expression of class II, B7-1, and several other cell surface molecules, though to a lesser extent. Immature and mature DC can be also easily distinguished by morphological analysis using light microscopy. See Mitchell et al., *Eur J Immunol* 28:1923-33, 1998; published erratum appears in *Eur J Immunol* 28:3891, 1998.

Example 3

Measurement of OVA-Specific CTL

To measure the induction of OVA CTL, splenocytes were isolated 7-8 days post injection with the DC, cultured for 5 days in the presence of OVA mRNA transfected DC and assayed for the presence of OVA-specific CTL using a standard cytotoxicity assay. See e.g. Volgmann T, Klein-Struckmeier A, Mohr H., "A fluorescence-based assay for quantitation of lymphokine-activated killer cell activity", *J Immunol Methods* (1989) 119:45-51.

Example 4

Effect of "Priming" Tissue on Immunostimulatory Properties of Immature DC

Figure 3:
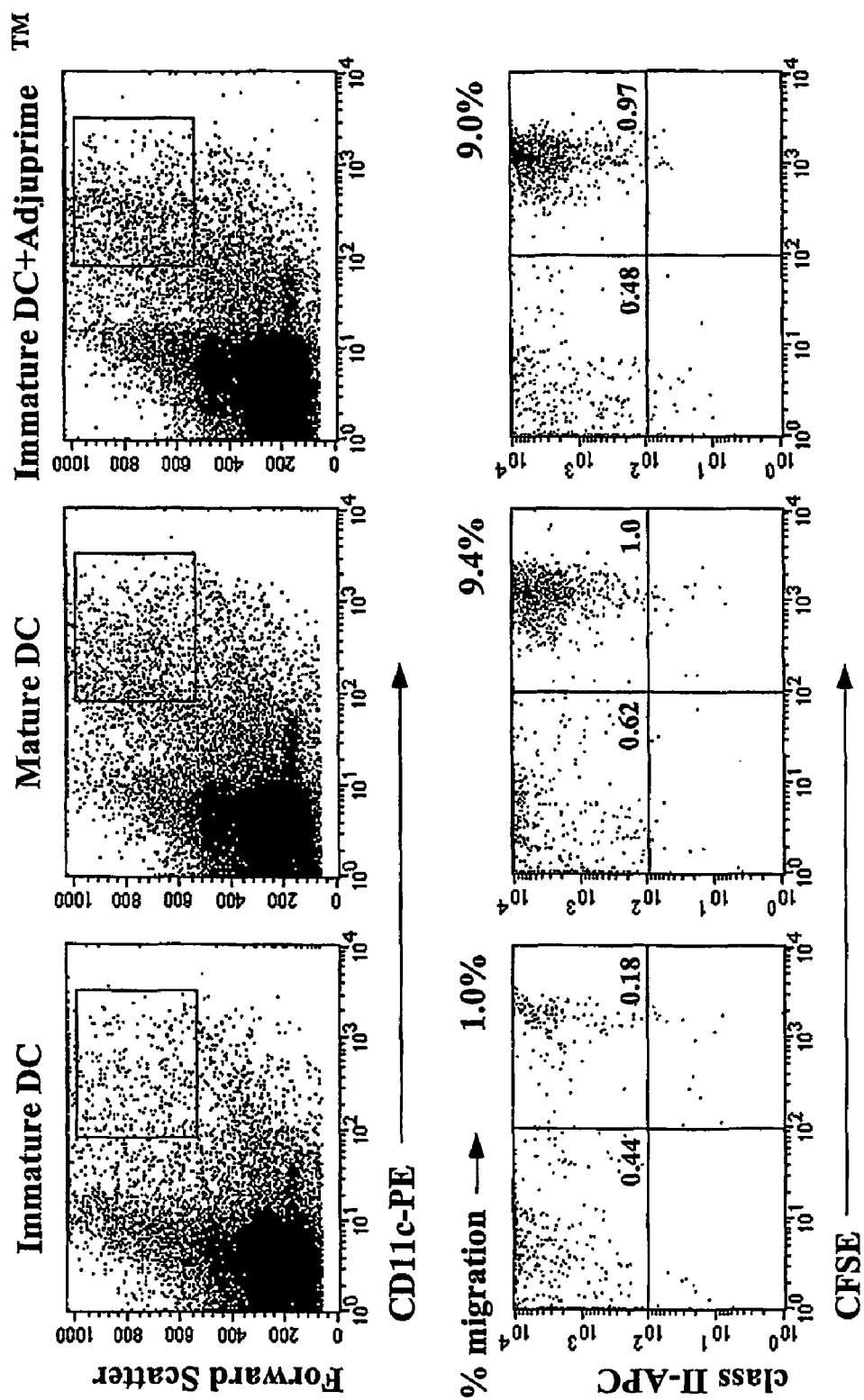
FIG. 3 depicts flow cytometry analysis of the migration of DC to the draining lymph nodes. Immature or mature DC were transfected with OVA mRNA and incubated with CFSE. Cells were washed and $3 \times 10^5$ DC were injected into the ear pinna. In one instance, 15 minutes prior to injection of immature DC the mice were injected with ADJUPRIME™ adjuvant (available from Pierce Biotechnology, Inc., Rockford, Ill. United States of America). Twenty-four hours post infection of the DC, the draining auricular lymph node was dissected, a cell suspension generated, and cells were analyzed by flow cytometry. To identify the DC subset, cells gated for CD11c$^+$ granular cells (upper panels) were analyzed for class II expression and CFSE content (lower panels). Injected DC are class II$^{high}$ CFSE$^+$ (UR quadroon) whereas the class II$^{high}$- CFSE$^-$ represent the resident and newly arrived, endogenous, DC (UL quadroon). The percentages shown in the UR quadroons constitute the percentage of CFSE$^+$ DC injected into the ear found in the lymph node.

Immature DC transfected with OVA mRNA were injected into the ear pinna that was either untreated or pretreated with ADJUPRIME™ adjuvant. As a positive control, mature DC transfected with OVA mRNA were injected into ear pinna that was not pretreated with ADJUPRIME™ adjuvant. As shown in FIG. 3, the migration properties of the injected DC was measured. To monitor DC migration in vivo, the DC were incubated with the vital dye CFSE prior to injection. The injected and resident lymph node DC were identified as $CD11c^+classII^{high}CFSE^+$ and $CD11c^+classII^{high}CFSE^-$ cells, respectively.

In mice injected with immature DC, about 1.5% of the total lymph node DC population included the $CFSE^+$ injected DC and about 1.2% of the DC injected into the ear migrated to the lymph node. In contrast, in lymph nodes derived from mice injected with either mature DC or immature DC that were injected into ADJUPRIME™ adjuvant primed site, about 50% of the lymph node DC were derived from the injected population and 15% or 13% of the ear injected DC migrated to the lymph node. Thus, the injection of immature DC into the ADJUPRIME™ adjuvant treated "primed" tissue results in their maturation and migration to the draining lymph nodes. The small but detectable presence of class $II^{high}$ $CFSE^+$ DC in the lymph nodes of mice injected with immature DC in the absence of adjuvant pretreatment (1.2%, FIG. 3, lower left panel) could be due to either maturation of some immature DC in the process of injection, or more likely due to the presence of a small population of mature (class $II^{high}$) DC in the day 6 population (see FIG. 2).

Example 5

Induction of OVA CTL in Mice Immunized with OVA mRNA Transfected DC

Figure 4:
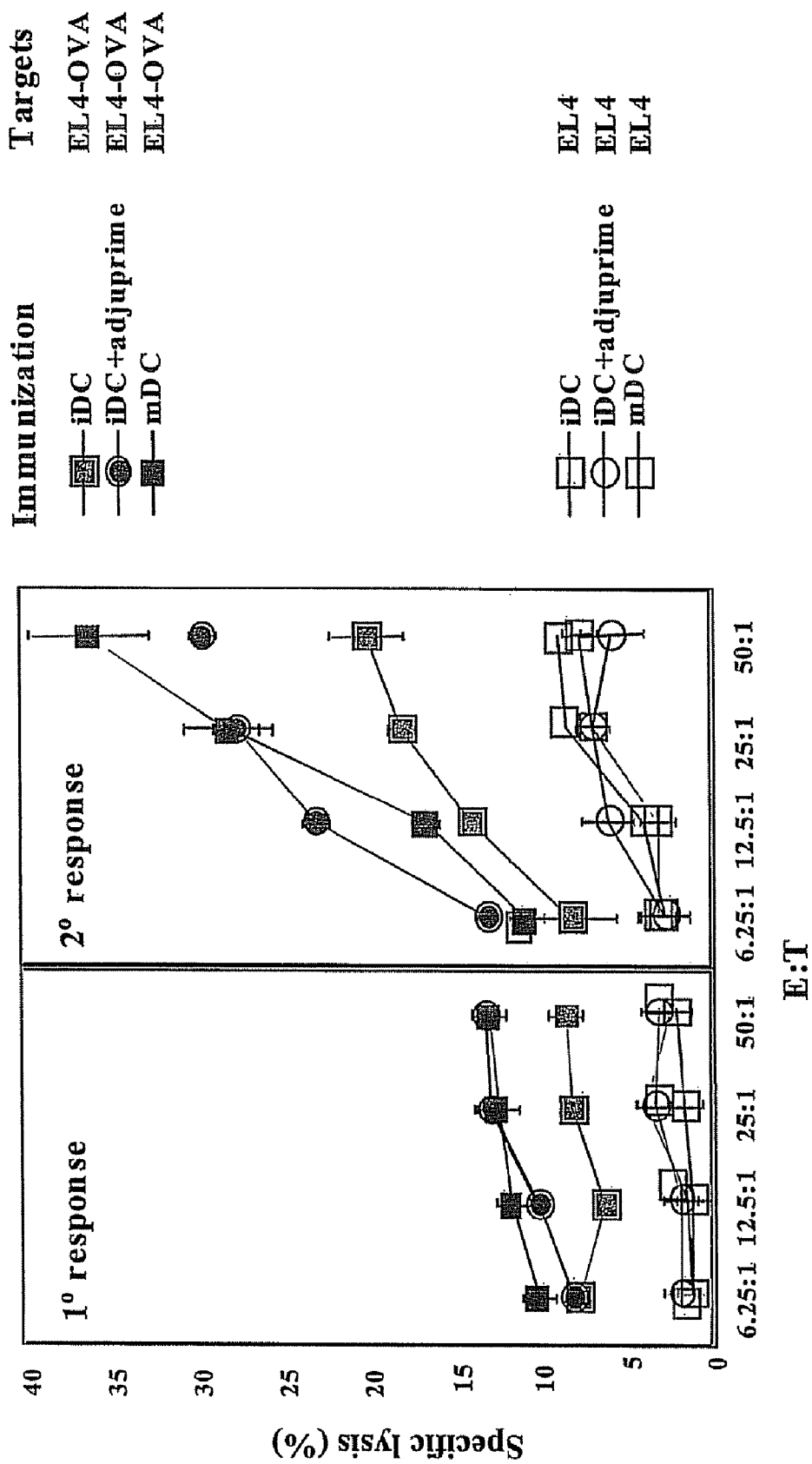
FIG. 4 is a graph depicting the induction of OVA CTL in mice immunized with OVA mRNA transfected DC. Mice were immunized as described in FIG. 3 except that DC were not stained with CFSE. Splenocytes were harvested after 8 days and either analyzed directly for CTL (left panel) or incubated for 5 days in the presence of OVA mRNA transfected DC (right panel). CTL activity was determined using a standard cytotoxicity assay and OVA-expressing EL-4 cells, and EL-4 cells as targets. (iDC: immature DC; mDC: mature DC; solid gray square: iDC and OVA-expressing EL-4 cells; solid black oval: iDC+ADJUPRIME™ adjuvant and OVA-expressing EL-4 cells; solid black square: mDC and OVA-expressing EL-4 cells; open gray square: iDC and EL4 cells; open black oval: iDC+ADJUPRIME™ adjuvant and EL4 cells; open black square: mDC and EL4 cells).

Whether the immature DC injected into the "primed" tissue will acquire strong immunostimulatory capacity in vivo was tested. The induction of OVA CTL in mice immunized with OVA mRNA transfected DC as described for FIG. 3 was measured. As shown in FIG. 4, mature DC are more potent than immature DC in stimulating a CTL response. The CTL activity stimulated by the immature DC could be attributed to the presence of (class $II^{high}$) DC in the draining lymph nodes (see FIG. 3) that could represent a subset of mature DC in the day 6 immature DC preparations. Injection of immature DC into the adjuvant pretreated site induces a CTL response comparable to that seen with mature DC, as seen both when CTL are analyzed directly (left panel, 1° response) as well as following in vitro stimulation (right panel, 2° response). Thus, judging from the migration and immunostimulatory capacities of the injected DC, injection of immature DC into "primed" sites can induce their functional maturation to an immunopotent APC.

Example 6

Induction of OVA-Specific CTL with Immature DC

In Situ Maturation with Imiquimod

Figure 5:
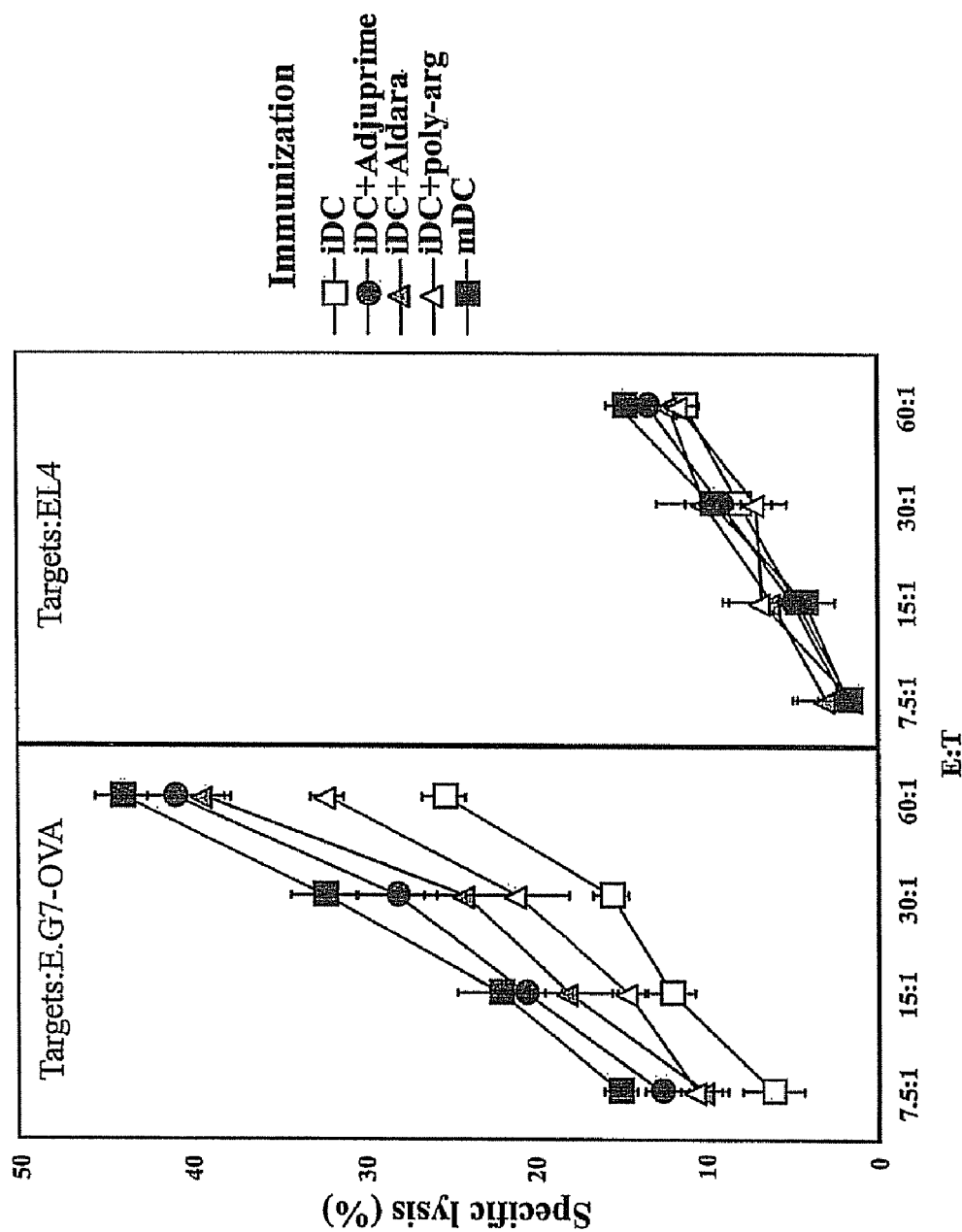
FIG. 5 is a graph depicting the induction of OVA specific CTL with immature DC during in situ maturation with Imiquimod (sold under the trademark ALDARA™ by 3M of St. Paul, Minn., United States of America) and poly arginine. Experimental details are as described for FIG. 4. Here, in addition to ADJUPRIME™ adjuvant, Imiquimod (ALDARA™ brand) and poly arginine (poly-arg) were used to induce local "inflammation" prior to immunization with the OVA mRNA transfected immature DC. The ALDARA™ clinically approved cream formulation of Imiquimod was applied to the ear surface 15 minutes prior to DC injection. Poly-arg was injected into the ear pinna (50 µl; 100 µg/ml) 15 minutes prior to DC injection. (open square: iDC; solid circle: iDC+ADJUPRIME™ adjuvant; solid triangle: iDC+ALDARA™ adjuvant; open triangle: iDC+poly-arginine; solid square: mDC).

To further assess the generality of the in situ maturation approach, two additional agents were tested. A cream formulation of Imiquimod sold under the trademark ALDARA™ by 3M of St. Paul, Minn. United States of America, which exhibits potent Th1 inducing immunity (see e.g., Weeks et al., *J Interferon Res* 14:81-5, 1994; Testerman et al., *J Leukoc Biol* 58:365-72, 1995; Megyeri et al., *Mol Cell Biol* 15:2207-18, 1995; Suzuki et al., *J Invest Dermatol* 114:135-41, 2000) and which is approved for clinical use, was employed. Poly arginine (poly-arg) was shown to enhance the immunogenicity and anticancer activities of peptide antigens (see e.g., Schmidt et al., *Proc Natl Acad Sci USA* 94:3262-7, 1997; Mattner et al., *Cancer Res* 62:1477-80, 2002). FIG. 5 confirms the results shown in FIG. 4 that immature DC injected into a site pretreated with ADJUPRIME™ adjuvant stimulate a potent CTL response comparable to the CTL response stimulated by mature DC. In addition, FIG. 5 shows that pretreatment of the injection site with either ALDARA™ adjuvant or poly-arg potentiates the CTL response stimulated by immature DC. ALDARA™ adjuvant is almost as effective as ADJUPRIME™ adjuvant whereas the effect of poly-arg is small. ALDARA™ adjuvant was applied to the ear surface 15 min prior to DC injection. Poly-arg was injected into the ear pinna (50 μl; 100 μg/ml) 15 minutes prior to DC injection.

The interval between adjuvant application and injection of immature DC was 15 minutes, although this short interval might be suboptimal. To test whether modifying the experimental conditions could improve the immunostimulatory capacity of immature DC, in the next experiment the interval between adjuvant application and DC injection was extended to 4 hours. Imiquimod was used in this experiment because it is a clinically approved reagent. Migration of immature DC, mature DC, and immature DC injected into the Imiquimod pretreated site, determined as shown in FIG. 3, was 1.2%, 7.2 and 9.2% of the injected DC, respectively, confirming the observation shown in FIG. 3 that injection of immature DC into adjuvant "primed" tissue enhances their migratory capacity.

Figure 6:
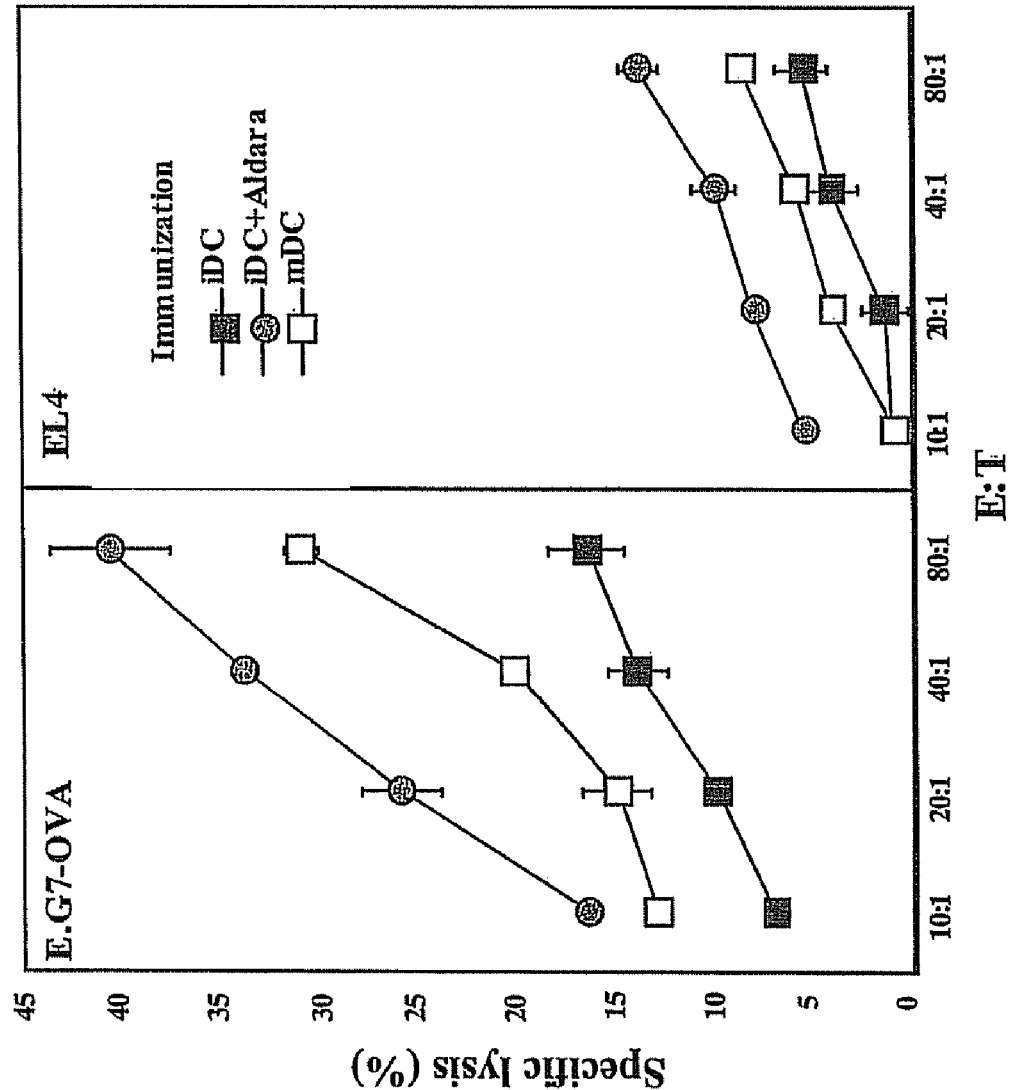
FIG. 6 is a graph depicting the induction of OVA specific CTL with immature DC during in situ maturation with Imiquimod (ALDARA™ brand). Experimental details are as described in FIGS. 3-5 except that Imiquimod (ALDARA™ brand) was applied 4 hours (instead of 15 minutes) before injection of the OVA mRNA transfected immature DC, (solid square: iDC; solid circle: iDC+ALDARA™ adjuvant; open square: mDC).

FIG. 6 shows that enhanced migration is also accompanied with a significantly improved immunostimulatory capacity. The immature DC injected into Imiquimod (ALDARA™ brand) pretreated sites stimulated a more potent CTL response than the ex vivo matured DC. This experiment (a) confirms and extends the observations shown in FIGS. 3-5 that injection of immature DC into "inflamed" tissue can induce their functional maturation, (b) suggest that optimization of the experimental conditions, and conceivably using other adjuvants, could improve the immunostimulatory capacity of the injected DC, and (c) the in situ DC maturation approach could generate DC with immunostimulatory capacity which is superior to that of ex vivo matured DC.

REFERENCES

The references listed below as well as all references cited in the specification are incorporated herein by reference to the extent that they supplement, explain, provide a background for or teach methodology, techniques and/or compositions employed herein.

Asseman C, Mauze S, Leach M W, Coffman R L & Powrie F (1999) An Essential Role for Interleukin 10 in the Function of Regulatory T Cells That Inhibit Intestinal Inflammation. *J Exp Med* 190:995-1004.

Ausubel F, ed (1995) *Short Protocols in Molecular Biology*, 3rd ed. Wiley, New York.

Banchereau J & Steinman R M (1998) Dendritic Cells and the Control of Immunity. *Nature* 392:245-252.

Banchereau J, Briere F, Caux C, Davoust J, Lebecque S, Liu Y J, Pulendran B & Palucka K (2000) Immunobiology of Dendritic Cells. *Annu Rev Immunol* 18:767-811.

Bell D, Young J W & Banchereau J (1999) Dendritic Cells. *Adv Immunol* 72:255-324.

Bumol T F, Marder P, DeHerdt S V, Borowitz M J & Apelgren L D (1988) Characterization of the Human Tumor and Normal Tissue Reactivity of the KS1/4 Monoclonal Antibody. *Hybridoma* 7:407-415.

Caux C, Dezutter-Dambuyant C, Schmitt D & Banchereau J (1992) GM-CSF and TNF-Alpha Cooperate in the Generation of Dendritic Langerhans Cells. *Nature* 360:258-261.

Cella M, Sallusto F & Lanzavecchia A (1997a) Origin, Maturation and Antigen Presenting Function of Dendritic Cells. *Curr Opin Immunol* 9:10-16.

Cella M, Engering A, Pinet V, Pieters J & Lanzavecchia A (1997b) Inflammatory Stimuli Induce Accumulation of MHC Class II Complexes on Dendritic Cells. *Nature* 388:782-787.

Chen Y, Kuchroo V K, Inobe J, Hafler D A & Weiner H L (1994) Regulatory T Cell Clones Induced by Oral Tolerance: Suppression of Autoimmune Encephalomyelitis. *Science* 265:1237-1240.

Dallal R M & Lotze M T (2000) The Dendritic Cell and Human Cancer Vaccines. *Curr Opin Immunol* 12:583-588.

Delneste Y, Herbault N, Galea B, Magistrelli G, Bazin I, Bonnefoy J Y & Jeannin P (1999) Vasoactive Intestinal Peptide Synergizes with TNF-Alpha in Inducing Human Dendritic Cell Maturation. *J Immunol* 163:3071-3075.

Elliott T, Townsend A & Cerundolo V (1990) Antigen Presentation. Naturally Processed Peptides. *Nature* 348:195-197.

Estin C D, Stevenson U, Kahn M, Hellstrom I & Hellstrom K E (1989) Transfected Mouse Melanoma Lines That Express Various Levels of Human Melanoma-Associated Antigen P97. *J Natl Cancer Inst* 81:445-448.

Falk K, Rotzschke O & Rammensee H G (1990) Cellular Peptide Composition Governed by Major Histocompatibility Complex Class I Molecules. *Nature* 348:248-251.

Falk K, Rotzschke O, Stevanovic S, Jung G & Rammensee H G (1991) Allele-Specific Motifs Revealed by Sequencing of Self-Peptides Eluted from MHC Molecules. *Nature* 351:290-296.

Fearon D T (1997) Seeking Wisdom in Innate Immunity. *Nature* 388:323-324.

Fearon D T & Locksley R M (1996) The Instructive Role of Innate Immunity in the Acquired Immune Response. *Science* 272:50-53.

Fisher F W & Cook N B (1998) *Fundamentals of Diagnostic Mycology*. W.B. Saunders, Philadelphia, Pa., United States of America.

Fong L & Engleman E G (2000) Dendritic Cells in Cancer Immunotherapy. *Annu Rev Immunol* 18:245-273.

Gilboa E, Nair S K & Lyerly H K (1998) Immunotherapy of Cancer with Dendritic-Cell-Based Vaccines. *Cancer Immunol Immunother* 46:82-87.

Glover D M & Hames B D (1995) *DNA Cloning: A Practical Approach*, 2nd ed. IRL Press at Oxford University Press, Oxford/New York.

Grouard G, Durand I, Filgueira L, Banchereau J & Liu Y J (1996) Dendritic Cells Capable of Stimulating T Cells in Germinal Centres. *Nature* 384:364-367.

Grouard G, Rissoan M C, Filgueira L, Durand I, Banchereau J & Liu Y J (1997) The Enigmatic Plasmacytoid T Cells Develop into Dendritic Cells with Interleukin (II)-3 and CD40-Ligand. *J Exp Med* 185:1101-1111.

Groux H, O'Garra A, Bigler M, Rouleau M, Antonenko S, de Vries J E & Roncarolo M G (1997) A CD4+ T-Cell Subset Inhibits Antigen-Specific T-Cell Responses and Prevents Colitis. *Nature* 389:737-742.

Hackstein H, Morelli A E & Thomson A W (2001) Designer Dendritic Cells for Tolerance Induction: Guided Not Misguided Missiles. *Trends Immunol* 22:437-442.

Heike M, Blachere N E, Wolfel T, Meyer zum Buschenfelde K H, Storkel S & Srivastava P K (1994) Membranes Activate Tumor- and Virus-Specific Precursor Cytotoxic T Lymphocytes In Vivo and Stimulate Tumor-Specific T Lymphocytes In Vitro: Implications for Vaccination. *J Immunother Emphasis Tumor Immunol* 15:165-174.

Henttu P & Vihko P (1989) cDNA Coding for the Entire Human Prostate Specific Antigen Shows High Homologies to the Human Tissue Kallikrein Genes. *Biochem Biophys Res Commun* 160:903-910.

Howell M D, Diveley J P, Lundeen K A, Esty A, Winters S T, Carlo D J & Brostoff S W (1991) Limited T-Cell Receptor Beta-Chain Heterogeneity among Interleukin 2 Receptor-Positive Synovial T Cells Suggests a Role for Superantigen in Rheumatoid Arthritis. *Proc Natl Acad Sci USA* 88:10921-10925.

Hsieh C S, Macatonia S E, Tripp C S, Wolf S F, O'Garra A & Murphy K M (1993) Development of Th1 CD4+ T Cells through IL-12 Produced by *Listeria*-Induced Macrophages. *Science* 260:547-549.

Inaba K, Inaba M, Naito M & Steinman R M (1993) Dendritic Cell Progenitors Phagocytose Particulates, Including *Bacillus* Calmette-Guerin Organisms, and Sensitize Mice to Mycobacterial Antigens In Vivo. *J Exp Med* 178:479-488.

Inaba K, Pack M, Inaba M, Sakuta H, Isdell F & Steinman R M (1997) High Levels of a Major Histocompatibility Complex II-Self Peptide Complex on Dendritic Cells from the T Cell Areas of Lymph Nodes. *J Exp Med* 186:665-672.

Inaba K, Inaba M, Romani N, Aya H, Deguchi M, Ikehara S, Muramatsu S & Steinman R M (1992) Generation of Large Numbers of Dendritic Cells from Mouse Bone Marrow Cultures Supplemented with Granulocyte/Macrophage Colony-Stimulating Factor. *J Exp Med* 176:1693-1702.

Israeli R S, Powell C T, Fair W R & Heston W D (1993) Molecular Cloning of a Complementary DNA Encoding a Prostate-Specific Membrane Antigen. *Cancer Res* 53:227-230.

Janeway C A, Jr. (1989) Approaching the Asymptote? Evolution and Revolution in Immunology. *Cold Spring Harb Symp Quant Biol* 54:1-13.

Jiang W, Swiggard W J, Heufler C, Peng M, Mirza A, Steinman R M & Nussenzweig M C (1995) The Receptor DEC-205 Expressed by Dendritic Cells and Thymic Epithelial Cells Is Involved in Antigen Processing. *Nature* 375:151-155.

Jonuleit H, Schmitt E, Steinbrink K & Enk A H (2001) Dendritic Cells as a Tool to Induce Anergic and Regulatory T Cells. *Trends Immunol* 22:394-400.

Jonuleit H, Kuhn U, Muller G, Steinbrink K, Paragnik L, Schmitt E, Knop J & Enk A H (1997) Pro-inflammatory Cytokines and Prostaglandins Induce Maturation of Potent Immunostimulatory Dendritic Cells under Fetal Calf Serum-Free Conditions. *Eur J Immunol* 27:3135-3142.

Kimber I, Cumberbatch M, Dearman R J, Bhushan M & Griffiths C E (2000) Cytokines and Chemokines in the Initiation and Regulation of Epidermal Langerhans Cell Mobilization. *Br J Dermatol* 142:401-412.

Kitajima T, Ariizumi K, Bergstresser P R & Takashima A (1996) A Novel Mechanism of Glucocorticoid-Induced Immune Suppression: The Inhibition of T Cell-Mediated Terminal Maturation of a Murine Dendritic Cell Line. *J Clin Invest* 98:142-147.

Kumar V, Cotran R S & Robbins S L (1997) *Basic Pathology*, 6th ed. W.B. Saunders Co., Philadelphia, Pa., United States of America.

Le Gros G, Ben-Sasson S Z, Seder R, Finkelman F D & Paul W E (1990) Generation of Interleukin 4 (IL-4) Producing Cells In Vivo and In Vitro: IL-2 and IL-4 Are Required for In Vitro Generation of IL-4-Producing Cells. *J Exp Med* 172:921-929.

Lee H H, Morse S A & Olsvik Ø (1997) *Nucleic Acid Amplification Technologies: Application to Disease Diagnosis*. Birkhäuser Boston, Cambridge, Mass. United States of America.

Liu Y J, Grouard G, de Bouteiller O & Banchereau J (1996) Follicular Dendritic Cells and Germinal Centers. *Int Rev Cytol* 166:139-179.

Liu Y J, Xu J, de Bouteiller O, Parham C L, Grouard G, Djossou O, de Saint-Vis B, Lebecque S, Banchereau J & Moore K W (1997) Follicular Dendritic Cells Specifically Express the Long CR2/CD21 Isoform. *J Exp Med* 185:165-170.

Mai K T, Isotalo P A, Green J, Perkins D G, Morash C & Collins J P (2000) Incidental Prostatic Adenocarcinomas and Putative Premalignant Lesions in Turp Specimens Collected before and after the Introduction of Prostate-Specific Antigen Screening. *Arch Pathol Lab Med* 124:1454-1456.

Manetti R, Parronchi P, Giudizi M G, Piccinni M P, Maggi E, Trinchieri G & Romagnani S (1993) Natural Killer Cell Stimulatory Factor (Interleukin 12 [IL-12]) Induces T Helper Type 1 (Th1)-Specific Immune Responses and Inhibits the Development of IL-4-Producing Th Cells. *J Exp Med* 177:1199-1204.

Maraskovsky E, Brasel K, Teepe M, Roux E R, Lyman S D, Shortman K & McKenna H J (1996) Dramatic Increase in the Numbers of Functionally Mature Dendritic Cells in Flt3 Ligand-Treated Mice: Multiple Dendritic Cell Subpopulations Identified. *J Exp Med* 184:1953-1962.

Mattner, F, Fleitmann, J K, Lingnau, K, Schmidt, W, Egyed, A, Fritz, J, Zauner, W, Wittmann, B, Gorny, I, Berger, M, Kirlappos, H, Otava, A, Birnstiel, M L, and Buschle, M (2002) Vaccination with poly-L-arginine as immunostimulant for peptide vaccines: induction of potent and long-lasting T-cell responses against cancer antigens. *Cancer Res* 62:1477-80.

Matsumoto M, Fu Y X, Molina H, Huang G, Kim J, Thomas D A, Nahm M H & Chaplin D D (1997) Distinct Roles of Lymphotoxin Alpha and the Type I Tumor Necrosis Factor (TNF) Receptor in the Establishment of Follicular Dendritic Cells from Non-Bone Marrow-Derived Cells. *J Exp Med* 186:1997-2004.

Megyeri, K, Au, W C, Rosztoczy, I, Raj, N B, Miller, R L, Tomai, M A, and Pitha, P A (1995) Stimulation of interferon and cytokine gene expression by imiquimod and stimulation by Sendai virus utilize similar signal transduction pathways. *Mol Cell Biol* 15:2207-18.

Mitchell, D A, Nair, S K, and Gilboa, E (1998) Dendritic cell/macrophage precursors capture exogenous antigen for MHC class I presentation by dendritic cells. *Eur J Immunol* 28:1923-33, (published erratum appears in *Eur J Immunol* 28:3891, 1998).

Moll H, Fuchs H, Blank C & Rollinghoff M (1993) Langerhans Cells Transport *Leishmania Major* from the Infected Skin to the Draining Lymph Node for Presentation to Antigen-Specific T Cells. *Eur J Immunol* 23:1595-1601.

Morse M A, Lyerly H K, Gilboa E, Thomas E & Nair S K (1998) Optimization of the Sequence of Antigen Loading and CD40-Ligand-Induced Maturation of Dendritic Cells. *Cancer Res* 58:2965-2968.

Nair S K, Boczkowski D, Morse M, Cumming R I, Lyerly H K & Gilboa E (1998) Induction of Primary Carcinoembryonic Antigen (CEA)-Specific Cytotoxic T Lymphocytes In Vitro Using Human Dendritic Cells Transfected with RNA. *Nat Biotechnol* 16:364-369.

Natali P G, Roberts J T, Difilippo F, Bigotti A, Dent P B, Ferrone S & Liao S K (1987) Immunohistochemical Detection of Antigen in Human Primary and Metastatic Melanomas by the Monoclonal Antibody 140.240 and Its Possible Prognostic Significance. *Cancer* 59:55-63.

Nestle F O, Alijagic S, Gilliet M, Sun Y, Grabbe S, Dummer R, Burg G & Schadendorf D (1998) Vaccination of Melanoma Patients with Peptide- or Tumor Lysate-Pulsed Dendritic Cells. *Nat Med* 4:328-332.

Nijman H W, Kleijmeer M J, Ossevoort M A, Oorschot V M, Vierboom M P, van de Keur M, Kenemans P, Kast W M, Geuze H J & Melief C J (1995) Antigen Capture and Major Histocompatibility Class II Compartments of Freshly Isolated and Cultured Human Blood Dendritic Cells. *J Exp Med* 182:163-174.

Nohria A & Rubin R H (1994) Cytokines as Potential Vaccine Adjuvants. *Biotherapy* 7:261-269.

Oksenberg J R, Stuart S, Begovich A B, Bell R B, Erlich H A, Steinman L & Bernard C C (1990) Limited Heterogeneity of Rearranged T-Cell Receptor V Alpha Transcripts in Brains of Multiple Sclerosis Patients. *Nature* 345:344-346.

Paliard X, West S G, Lafferty J A, Clements J R, Kappler J W, Marrack P & Kotzin B L (1991) Evidence for the Effects of a Superantigen in Rheumatoid Arthritis. *Science* 253:325-329.

PCT International Publication No. WO 00/09151

PCT International Publication No. WO 00/46248

Perez M S & Walker L E (1989) Isolation and Characterization of a cDNA Encoding the KS1/4 Epithelial Carcinoma Marker. *J Immunol* 142:3662-3667.

Pierre P, Turley S J, Gatti E, Hull M, Meltzer J, Mirza A, Inaba K, Steinman R M & Mellman I (1997) Developmental Regulation of MHC Class II Transport in Mouse Dendritic Cells. *Nature* 388:787-792.

Reddy A, Sapp M, Feldman M, Subklewe M & Bhardwaj N (1997) A Monocyte Conditioned Medium Is More Effective Than Defined Cytokines in Mediating the Terminal Maturation of Human Dendritic Cells. *Blood* 90:3640-3646.

Reis e Sousa C, Stahl P D & Austyn J M (1993) Phagocytosis of Antigens by Langerhans Cells In Vitro. *J Exp Med* 178:509-519.

Richards R (1995) A Compendium of Vaccine Adjuvants and Excipients. In: *Vaccine Design: The Subunit and Adjuvant Approach*. Plenum Press, New York.

Richardson M D & Warnock D W (1993) *Fungal Infection: Diagnosis and Management*. Blackwell Scientific Publications, Oxford/Boston.

Romagnani S (1992) Induction of Th1 and Th2 Responses: A Key Role for the 'Natural' Immune Response? *Immunol Today* 13:379-381.

Romani N, Reider D, Heuer M, Ebner S, Kampgen E, Eibl B, Niederwieser D & Schuler G (1996) Generation of Mature Dendritic Cells from Human Blood. An Improved Method with Special Regard to Clinical Applicability. *J Immunol Methods* 196:137-151.

Romani N, Gruner S, Brang D, Kampgen E, Lenz A, Trockenbacher B, Konwalinka G, Fritsch P O, Steinman R M & Schuler G (1994) Proliferating Dendritic Cell Progenitors in Human Blood. *J Exp Med* 180:83-93.

Rotzschke O, Falk K, Wallny H J, Faath S & Rammensee H G (1990a) Characterization of Naturally Occurring Minor Histocompatibility Peptides Including H-4 and H-Y. *Science* 249:283-287.

Rotzschke O, Falk K, Deres K, Schild H, Norda M, Metzger J, Jung G & Rammensee H G (1990b) Isolation and Analysis of Naturally Processed Viral Peptides as Recognized by Cytotoxic T Cells. *Nature* 348:252-254.

Saeboe-Larssen, S, Fossberg, E, and Gaudernack, G (2002) mRNA-based electrotransfection of human dendritic cells and induction of cytotoxic T lymphocyte responses against the telomerase catalytic subunit (hTERT). *J Immunol Methods* 259:191-203.

Sallusto F & Lanzavecchia A (1994) Efficient Presentation of Soluble Antigen by Cultured Human Dendritic Cells Is Maintained by Granulocyte/Macrophage Colony-Stimulating Factor Plus Interleukin 4 and Downregulated by Tumor Necrosis Factor Alpha. *J Exp Med* 179:1109-1118.

Sallusto F, Celia M, Danieli C & Lanzavecchia A (1995) Dendritic Cells Use Macropinocytosis and the Mannose Receptor to Concentrate Macromolecules in the Major Histocompatibility Complex Class II Compartment: Downregulation by Cytokines and Bacterial Products. *J Exp Med* 182:389-400.

Saloga J, Leung D Y, Reardon C, Giorno R C, Born W & Gelfand E W (1996) Cutaneous Exposure to the Superantigen Staphylococcal Enterotoxin B Elicits a T-Cell-Dependent Inflammatory Response. *J Invest Dermatol* 106:982-988.

Sambrook et al. e (1989) *Molecular Cloning: A Laboratory Manual*. Cold Spring Harbor Laboratory Press, Cold Spring Harbor, N.Y., United States of America.

Sato T, Maguire H C, Jr., Mastrangelo M J & Berd D (1995) Human Immune Response to DNP-Modified Autologous Cells after Treatment with a DNP-Conjugated Melanoma Vaccine. *Clin Immunol Immunopathol* 74:35-43.

Schena M (2000) *Microarray Biochip Technology*. Eaton Publishing, Natick, Mass., United States of America.

Schmidt, W, Buschle, M, Zauner, W, Kirlappos, H, Mechtler, K, Trska, B, and Birnstiel, M L (1997) Cell-free tumor antigen peptide-based cancer vaccines. *Proc Natl Acad Sci USA* 94:3262-7.

Shimoda K, van Deursen J, Sangster M Y, Sarawar S R, Carson R T, Tripp R A, Chu C, Quelle F W, Nosaka T, Vignali D A, Doherty P C, Grosveld G, Paul W E & Ihle J N (1996) Lack of IL-4-Induced Th2 Response and IgE Class Switching in Mice with Disrupted Stat6 Gene. *Nature* 380:630-633.

Silhavy T J, Berman M L, Enquist L W & Cold Spring Harbor Laboratory. (1984) *Experiments with Gene Fusions*. Cold Spring Harbor Laboratory, Cold Spring Harbor, N.Y., United States of America.

Skeiky Y A, Guderian J A, Benson D R, Bacelar O, Carvalho E M, Kubin M, Badaro R, Trinchieri G & Reed S G (1995) A Recombinant *Leishmania* Antigen That Stimulates Human Peripheral Blood Mononuclear Cells to Express a Th1-Type Cytokine Profile and to Produce Interleukin 12. *J Exp Med* 181:1527-1537.

Steinman R, Hoffman L & Pope M (1995) Maturation and Migration of Cutaneous Dendritic Cells. *J Invest Dermatol* 105:2S-7S.

Steinman R M (1991) The Dendritic Cell System and Its Role in Immunogenicity. *Annu Rev Immunol* 9:271-296.

Steinman R M, Turley S, Mellman I & Inaba K (2000) The Induction of Tolerance by Dendritic Cells That Have Captured Apoptotic Cells. *J Exp Med* 191:411-416.

Storch G A (2000) *Essentials of Diagnostic Virology*. Churchill Livingstone, New York.

Suzue K, Zhou X, Eisen H N & Young R A (1997) Heat Shock Fusion Proteins as Vehicles for Antigen Delivery into the Major Histocompatibility Complex Class I Presentation Pathway. *PNAS* 94:13146-13151.

Suzuki, H, Wang, B, Shivji, G M, Toto, P, Amerio, P, Tomai, M A, Miller, R L, and Sauder, D N (2000) Imiquimod, a topical immune response modifier, induces migration of Langerhans cells. *J Invest Dermatol* 114:135-41.

Svensson M, Stockinger B & Wick M J (1997) Bone Marrow-Derived Dendritic Cells Can Process Bacteria for MHC-I and MHC-II Presentation to T Cells. *J Immunol* 158:4229-4236.

Swain S L, Weinberg A D, English M & Huston G (1990) IL-4 Directs the Development of Th2-Like Helper Effectors. *J Immunol* 145:3796-3806.

Szabolcs P, Moore M A & Young J W (1995) Expansion of Immunostimulatory Dendritic Cells among the Myeloid Progeny of Human CD34+ Bone Marrow Precursors Cultured with c-Kit Ligand, Granulocyte-Macrophage Colony-Stimulating Factor, and TNF-Alpha. *J Immunol* 154:5851-5861.

Tailor P G, Govindan M V & Patel P C (1990) Nucleotide Sequence of Human Prostatic Acid Phosphatase Determined from a Full-Length cDNA Clone. *Nucleic Acids Res* 18:4928.

Testerman, T L, Gerster, J F, Imbertson, L M, Reiter, M J, Miller, R L, Gibson, S J, Wagner, T L, and Tomai, M A (1995) Cytokine induction by the immunomodulators imiquimod and S-27609. *J Leukoc Biol* 58:365-72.

Tsai V, Southwood S, Sidney J, Sakaguchi K, Kawakami Y, Appella E, Sette A & Celis E (1997) Identification of Subdominant CTL Epitopes of the GP100 Melanoma-Associated Tumor Antigen by Primary In Vitro Immunization with Peptide-Pulsed Dendritic Cells. *J Immunol* 158:1796-1802.

U.S. Patent Application Publication No. 2002/0019047
U.S. Patent Application Publication No. 2001/0024649
U.S. Patent Application Publication No. 2001/0026937
U.S. Patent Application Publication No. 2002/0004041
U.S. Pat. No. 5,643,786
U.S. Pat. No. 5,788,963
U.S. Pat. No. 5,853,719
U.S. Pat. No. 5,910,306
U.S. Pat. No. 5,977,081
U.S. Pat. No. 5,980,898
U.S. Pat. No. 5,994,126
U.S. Pat. No. 6,037,116
U.S. Pat. No. 6,080,725
U.S. Pat. No. 6,165,785
U.S. Pat. No. 6,210,672
U.S. Pat. No. 6,274,378
U.S. Pat. No. 6,306,388

Van Tendeloo, V F, Ponsaerts, P, Lardon, F, Nijs, G, Lenjou, M, Van Broeckhoven, C, Van Bockstaele, D R, and Berneman, Z N (2001) Highly efficient gene delivery by mRNA electroporation in human hematopoietic cells: superiority to lipofection and passive pulsing of mRNA and to electroporation of plasmid cDNA for tumor antigen loading of dendritic cells, *Blood* 98:49-56.

Vijayasaradhi S, Bouchard B & Houghton A N (1990) The Melanoma Antigen GP75 Is the Human Homologue of the Mouse B (Brown) Locus Gene Product. *J Exp Med* 171:1375-1380.

Vremec, D., & Shortman, K (1997) Dendritic cell subtypes in mouse lymphoid organs: cross-correlation of surface markers, changes with incubation, and differences among thymus, spleen, and lymph nodes. *J Immunol* 159:565-73.

Weeks, C E, & Gibson, S J (1994) Induction of interferon and other cytokines by imiquimod and its hydroxylated metabolite R-842 in human blood cells in vitro. *J Interferon Res* 14:81-5.

White D O & Fenner F (1994) *Medical Virology*, 4th ed. Academic Press, San Diego, Calif., United States of America.

Williams W V, Fang Q, Demarco D, VonFeldt J, Zurier R B & Weiner D B (1992) Restricted Heterogeneity of T Cell Receptor Transcripts in Rheumatoid Synovium. *J Clin Invest* 90:326-333.

Winzler C, Rovere P, Rescigno M, Granucci F, Penna G, Adorini L, Zimmermann V S, Davoust J & Ricciardi-Castagnoli P (1997) Maturation Stages of Mouse Dendritic Cells in Growth Factor-Dependent Long-Term Cultures. *J Exp Med* 185:317-328.

Wucherpfennig K W, Ota K, Endo N, Seidman J G, Rosenzweig A, Weiner H L & Hafler D A (1990) Shared Human T Cell Receptor V Beta Usage to Immunodominant Regions of Myelin Basic Protein. *Science* 248:1016-1019.

Yu Q & Lian L J (1991) [Ca125 and Radioimmunoimaging in Monitoring of Epithelial Ovarian Carcinoma]. *Zhonghua Fu Chan Ke Za Zhi* 26:235-238, 252.

It will be understood that various details of the invention can be changed without departing from the scope of the invention. Furthermore, the foregoing description is for the purpose of illustration only, and not for the purpose of limitation—the invention being defined by the claims appended hereto.

What is claimed is:

1. A method for eliciting an immune response in a subject, the method comprising:
    (a) administering a biological response modifier consisting of imiquimod and a pharmaceutically acceptable carrier to a subject at a site to induce local inflammation at the site; followed by
    (b) administering antigen-loaded immature dendritic cells to the subject at the inflamed site by intradermal, subcutaneous or intramuscular injection;
whereby an immune response to the antigen is generated in the subject and wherein said antigen(s) are derived from a tumor or pathogen.

2. The method of claim 1, wherein the immature dendritic cells are autologous to the subject.

3. The method of claim 1, wherein the antigen comprises an exogenous antigen.

4. The method of claim 1 wherein the biological response modifier is administered to the site between 15 and 60 minutes before the immature dendritic cells are administered to the site.

5. The method of claim 1 wherein the biological response modifier is administered to the site between 1 and 3 hours before the immature dendritic cells are administered to the site.

6. The method of claim 1, wherein the biological response modifier is administered to the site between 3 and 5 hours before the immature dendritic cells are administered to the site.

7. The method of claim 1, wherein the biological response modifier is administered to the site between 5 and 8 hours before the immature dendritic cells are administered to the site.

8. The method of claim 1, wherein the biological response modifier is administered to the site more than 8 hours before the immature dendritic cells are administered to the site.

9. The method of claim 1, wherein the subject is a mammal.

10. The method of claim 9, wherein the mammal is a human.

11. The method of claim 1, wherein said dendritic cells are transfected with RNA encoding said antigen.

* * * * *